Figure 1:
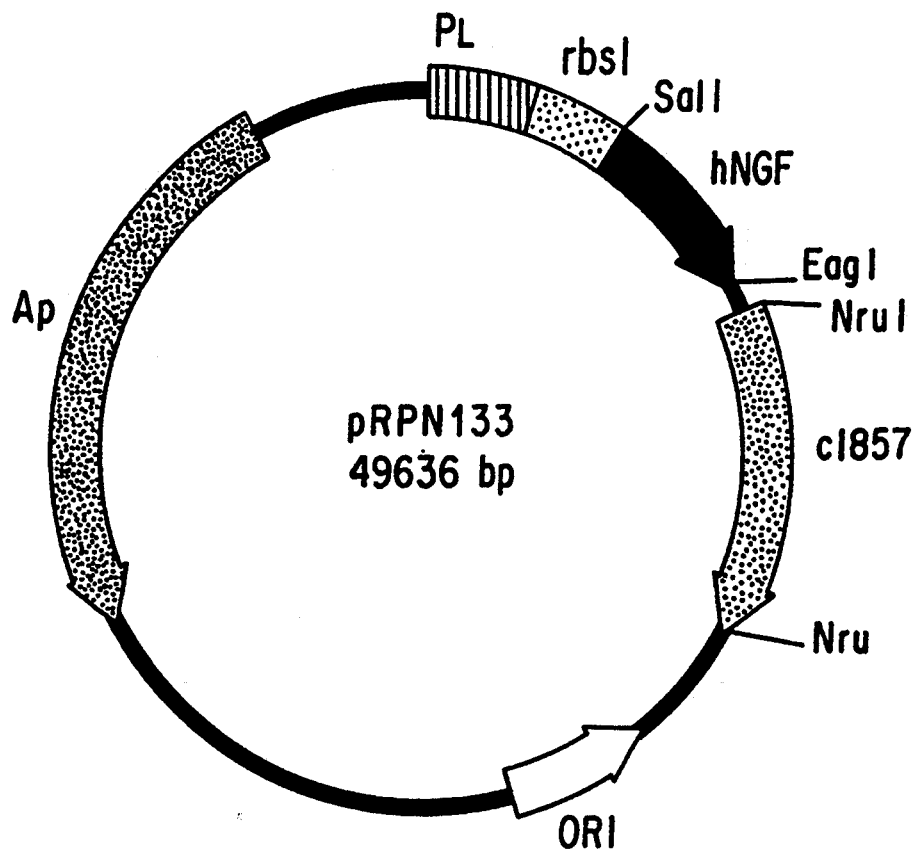

United States Patent [19]

Panayotatos et al.

[11] Patent Number: 5,389,529
[45] Date of Patent: Feb. 14, 1995

[54] MODIFIED LAMβ SIGNAL SEQUENCE AND PROCESSES FOR PRODUCING RECOMBINANT NEUROTROPHINS

[75] Inventors: Nikos Panayotatos, Orangeburg; James P. Fandl, La Grangeville, both of N.Y.

[73] Assignee: Regeneron Pharmaceuticals, Inc., Tarrytown, N.Y.

[21] Appl. No.: 796,106

[22] Filed: Nov. 21, 1991

Related U.S. Application Data

[63] Continuation-in-part of Ser. No. 715,185, Jun. 12, 1991, abandoned.

[51] Int. Cl.$^6$ .............................................. C12N 15/11
[52] U.S. Cl. ........................ 435/69.8; 435/172.1; 435/320.1; 435/69.4; 435/71.2; 536/23.1; 536/23.4; 935/48
[58] Field of Search ................ 435/69.4, 69.7, 69.8, 435/71.2, 172.1, 320.1; 530/399

[56] References Cited

U.S. PATENT DOCUMENTS

| | | | |
|---|---|---|---|
| 4,511,502 | 4/1985 | Builder et al. | 260/112 R |
| 4,620,948 | 11/1986 | Builder et al. | 530/419 |
| 4,680,262 | 7/1987 | Bochner et al. | 435/68 |
| 4,734,362 | 3/1988 | Hung et al. | 435/68 |
| 4,758,512 | 7/1988 | Goldberg et al. | 435/68 |
| 4,961,969 | 10/1990 | Hershenson et al. | 435/69.51 |

FOREIGN PATENT DOCUMENTS

| | | |
|---|---|---|
| 0121338 | 10/1984 | European Pat. Off. |
| 0333574 | 9/1989 | European Pat. Off. |
| 0370171 | 5/1990 | European Pat. Off. |
| 0386752 | 9/1990 | European Pat. Off. |
| 0398753 | 11/1990 | European Pat. Off. |
| 0414151 | 2/1991 | European Pat. Off. |
| 0450386 | 10/1991 | European Pat. Off. |
| WO89/01940 | 3/1989 | WIPO |
| WO90/06764 | 6/1990 | WIPO |
| WO91/03568 | 3/1991 | WIPO |
| WO91/03569 | 3/1991 | WIPO |
| WO92/05254 | 4/1992 | WIPO |

OTHER PUBLICATIONS

Ip et al., 1992, "Mammalian Neurotrophin-4: Structure, Chromosomal Localization, Tissue Distribution, and Receptor Specificity," *Proc. Natl. Acad. Sci. USA* 89:3060–3064.

Stader et al., 1990, Methods In Enzymology, vol. 185 "Engineering *Escherichia coli* to Secrete Heterologous Gene Products", pp. 166–187.

Berkemeier et al., 1991, "Neurotrophin-5: A Novel Neurotrophin that activates trk and trkB": Neuron 7:857–866.

Chapter 4, p. 77, *Biochemistry*, Second Edition, "The Molecular Basis of Cell Structure and Function", Ed. A. L. Lehninger (1977).

Bruce, G., and G. Heinrich, 1989, "Production and Characterization of Biologically Active Recombinant Human Nerve Growth Factor," *Neurobiology of Aging*, 10:89–94.

Denéfle, P., et al., 1989, "Heterologous Protein Export in *Escherichia coli*: Influence of Bacterial Signal Peptides on the Export of Human Interleukin 1β," *Gene*, 85:499–510.

Dicou, E., et al., 1989, "Synthesis of Chimeric Mouse Nerve Growth Factor Precursor and Human β-Nerve Growth Factor in *Escherichia Coli*: Immunological Properties," *Journal of Neuroscience Research*, 22:13–19.

Evan, G. I., et al., 1985, "Isolation of Monoclonal Antibodies Specific for Human c-myc Proto-Oncogene Product," *Mol. Cell. Biol.*, 5:3610–16.

Fonnum, F. 1975, "A Rapid Radiochemical Method for the Determination of Choline Acetyltransferase," *J. Neurochem.*, 24:407–409.

(List continued on next page.)

*Primary Examiner*—Robert J. Hill, Jr.
*Assistant Examiner*—Lorraine M. Spector
*Attorney, Agent, or Firm*—Pennie & Edmonds

[57] ABSTRACT

Signal sequences based on LamB have been constructed. These signal sequences facilitate both the synthesis and secretion of neurotrophins in E. coli.

6 Claims, 18 Drawing Sheets

OTHER PUBLICATIONS

Goff, S. A., et al., 1984, "Heat Shock Regulatory Gene *htp*R Influences Rates of Protein Degradation and Expression of the *lon* Gene in *Escherichia coli*," *Proc. Natl. Acad. Sci. USA*, 81:6647–51.

Halbook, F. et al., 1991, "Evolutionary Studies of the Nerve Growth Factor Family Reveal a Novel Member Abundantly Expressed in Xenopus Ovary," *Neuron*, 6:845–858.

Hedgpeth, J., et al., 1980, "DNA Sequence Encoding the $NH_2$Terminal Peptide Involved in Transport of λ Receptor, an *Escherichia coli* Secretory Protein," *Proc. Natl. Acad. Sci. USA*, 77:2621–2625.

Hohn, A. et al., 1990, "Identification and Characterization of a Novel Member of The Nerve Growth Factor/Brain–Derived Neurotrophic Factory Family," *Nature*, 344:339–341.

Hu, G., et al., 1990, "Comparison of Expression and Folding of Mouse Recombinant β–Nerve Growth Factor (NGF) in Bacterial Systems," *Abstracts: Soc. for Neuroscience, 20th Ann. Mtg.*, 16:343.16.

Hu, G., and K. E. Neet, 1988, "Expression of the cDNA for Mouse β–Nerve Growth Factor Protein in *Escherichia coli*,"*Gene*, 70:57–65.

Ibanez, C. F., et al., 1990, "Structure-function Studies of Nerve Growth Factor: Functional Importance of Highly Conserved Amino Acid Residues," *EMBO J.*, 9:1477–83.

Iwai, S., et al., 1986, "Synthesis of Genes for Human Nerve Growth Factor and Its Fused Protein," *Chem. Pharm. Bull.*, 34:4724–30.

Kaisho, Y., et al., 1990, "Cloning and Expression of a cDNA Encoding a Novel Human Neurotrophic Factor," *FEBS Letters*, 266:187–191.

Kanaya, E., et al., 1989, "Synthesis and Secretion of Human Nerve Growth Factor by *Saccharomyces cerevisiae*," *Gene*, 83:65–74.

Kawaguchi, Y., et al., 1984, "Renaturation and Activation of Calf Prochymosin Produced in an Insoluble Form in *Escherichia coli*," *J. of Biotechnology*, 1:307–315.

Leibrock, J., et al., 1989, "Molecular Cloning and Expression of Brain–derived Neurotrophic Factor," *Nature*, 341:149–52.

Maisonpierre, P. C., et al., 1990, "Neurotrophin-3: A Neurotrophic Factor Related to NGF and BDNF," *Science*, 247:1446–51.

Marston, F. A. O., et al., 1984, "Purification of Calf Prochymosin (Prorennin) Synthesized in *Escherichia coli*," *Bio/Technology*, Sep. 1984, pp. 800–804.

Meier, R. et al., 1986, "Molecular Cloning of Bovine and Chick Nerve Growth Factor (NGF): Delineation of Conserved and Unconserved Domains and their Relationship to the Biological Activity and Antigenicity of NGF," *EMBO J.*, 5:1489–1493.

Miller, K. W., et al., 1989, "Secretory Leukocyte Protease Inhibitor Binding to mRNA and DNA as a Possible Cause of Tosicity to *Escherichia coli*," *J. Bacteriol.*, 171(4):2166–72.

Obukowicz, M. G., et al., 1988, "Secretion and Export of IGF-1 in *Escherichia coli* Strain JM101," *Mol. Gen. Genet.*, 215:19–25.

Panayotatos, N., 1987, "Engineering on Efficient Expression System," *Plasmids–A Practical Approach*, (Hardy, K., ed.), IRL Press, Oxford/Washington, D.C.

Rosenthal, A. et al., 1990, "Primary Structure and Biological Activity of a Novel Human Neurotrophic Factor," *Neuron*, 4:767–773.

Sambrook, J., et al., 1989, *Molecular Cloning, A Laboratory Manual*, Cold Spring Harbor Laboratory Press, Cold Spring Harbor, New York.

Schwarz, M. A. et al., 1989, "Isolation and Sequence of a cDNA Clone of β–Nerve Growth Factor From the Guinea Pig Prostate Gland," *J. of Neurochemistry*, 52:1203–1209.

Scott, J. et al., 1983, "Isolation and Nucleotide Sequence of a cDNA Encoding the Precursor of Mouse Nerve Growth Factor," *Nature*, 302:538–540.

Selby, M. J. et al., 1987, "Cobra Nerve Growth Factor: Structure and Evolutionary Comparison," *J. of Neurosci. Res.*, 18:293–298.

Tsuji, T., et al., 1987, "Characterization of Disulfide Bonds in Recombinant Proteins: Reduced Human Interleukin 2 in Inclusion Bodies and Its Oxidative Refolding," *Biochemistry*, 26:3129–34.

Twigg, A. J., and D. Sherratt, 1980, "Trans–complementable Copy–Number Mutants of Plasmid ColE1," *Nature*, 283:216–18.

Ullrich, A., et al., 1983, "Human β–nerve Growth Factor Gene Sequence Highly Homologous to That of Mouse," *Nature*, 303:821–25.

Wong, E. Y., et al., 1988, "Expression of Secreted Insulin–like Growth Factor-1 in *Escherichia coli*," *Gene*, 68:193–203.

```
>Espl
         |--|--|
              20                    40
     *         *           *            *
ATG ATG ATT ACT CTG CGC AAA CTT CCT CTG GCG GTT GCC GTC GCA GCG GGC
TAC TAC TAA TGA GAC GCG TTT GAA GGA GAC CGC CAA CGG CAG CGT CGC CCG
Met Met Ile Thr Leu Arg Lys Leu Pro Leu Ala Val Ala Val Ala Ala Gly>
 a   a   a   a   a   a   a   a   a   a   a   a   a   a   a   a   a > WT LAMBSS 60            *
     *         *
GTA ATG TCT GCT CAG GCA ATG GCT
CAT TAC AGA CGA GTC CGT TAC CGA
Val Met Ser Ala Gln Ala Met Ala>
 a   a   a   a   a   a   a   a > WT LAMBSS

FIG. 3A
```

FIG. 3B

```
     >BclI           >HindIII  >NheI                        >BspMI
      ---             ---       ---                          ---
       *               *         *                            *
                      20                                     40
C ATG ATG ATC ACA CTG CGT AAG CTT CCG CTA GCT GTA GCA GTA GCA GCA GGT
G TAC TAC TAG TGT GAC GCA TTC GAA GGC GAT CGA CAT CGT CAT CGT CGT CCA
  Met Met Ile Thr Leu Arg Lys Leu Pro Leu Ala Val Ala Val Ala Ala Gly>
   a   a   a   a   a   a   a   a  LAMB1 a   a   a   a   a   a   a   a >

>BamHI
                                        ---
                                 >SmaI  ---
                                  ---   ---
        >NcoI    >XmaI            ---   --- 80
         ---     ---              ---   ---  *
          *                       ---   ---
         60
GTA ATG TCT GCA CAG GCC ATG GCC CGG GAT CCC TAG
CAT TAC AGA CGT GTC CGG TAC CGG GCC CTA GGG ATC
Val Met Ser Ala Gln Ala Met Ala >
 a   a  LAMB1 a   a   a   a   a >
```

FIG. 3B

```
    >BclI            >HindIII  >NheI                              >BspMI
---|---*                  ---|---                  ---|---            ---|---
                          20       *                                  40       *
C ATG ATG ATC ACA CTG CGT AAG CTT CCG CTA GCT GTA GCA GCA GCA GGT
G TAC TAC TAG TGT GAC GCA TTC GAA GGC GAT CGA CAT CGT CGT CGT CCA
  Met Met Ile Thr Leu Arg Lys Leu Pro Leu Ala Val Ala Ala Ala Gly>
                                                                    >
  a   a   a   a   a   a   a   a  LAMB2  a   a   a   a   a   a   a
                                      >

>NcoI   >BalI                  >EagI                       >BamHI
       ---|---*   ---|---              ---|---                    ---|---
       60      *                       80      *
GTA ATG TCT GCA CAG GCC ATG GCC AGT CGG CCG AGG ATC CCT AG
CAT TAC AGA CGT GTC CGG TAC CGG TCA GCC GGC TCC TAG GGA TC
Val Met Ser Ala Gln Ala Met Ala Ser>
                                   >
  a   a  LAMB2   a   a   a   a   a
            >

FIG. 3C
```

```
           >BclI              >HindIII      >NheI      >ScaI       >NheI              >BspMI
         ---*---            ---*---       ---*---    ---*---    ---*---             ---*---
                              20                       40
C ATG ATG ATC ACA CTG CGT AAG CTT CCG CTA GCA GTA CTG CTA GCT GTA GCA
G TAC TAC TAG TGT GAC GCA TTC GAA GGC GAT CGT CAT CGA CGA GAT CGA CGT
  Met Met Ile Thr Leu Arg Lys Leu Pro Leu Ala Val Leu Leu Ala Val Ala>
  a   a   a   a   a   a   a   a   a   a   a   a   a   a   a   a   a     LAMB3

>NcoI  >BalI                       >EagI           >BamHI
                 ---*---                            ---*---         ---*---
         60               80                                 100
GTA GCA GGT GTA ATG TCT GCA GCC ATG GCC AGT CGG CCG GAG ATC CCT AG
CAT CGT CCA CAT TAC AGA CGT CGG TAC CGG TCA GCC GGC CTC CTA GGG ATC
Val Ala Gly Val Met Ser Ala Gln Ala Met Ala>
 a   a   a   a   a   a   a   a   a   a   a     LAMB3
```

FIG. 3D

```
      >BclI          >Hind3  >NheI         >NheI    >ScaI             >BspMI
       |--           |--     |--           |--      |--               |--
       |             |       |             |        |                 |
       *             *       *             *        *                 *
                            20                     40
C ATG ATG ATC ACA CTG CGT AAG CTT CCG CTA GCA GTA CTG CTA GCT GTA GCA
G TAC TAC TAG TGT GAC GCA TTC GAA GGC GAT CGT CAT GAC GAT CGA CAT CGT
  Met Met Ile Thr Leu Arg Lys Leu Pro Leu Ala Val Leu Leu Ala Val Ala>
   a   a   a   a   a   a   a   a   a  LAMB4 a   a   a   a   a   a   a >

>NcoI  >BalI          >EagI                        >BamH1
       |--   |--            |--                          |--
       |     |              |                            |
       *     *              *                            *
      60                                                100
GTA GCA GCA GGT GTA ATG TCT GCA GCC ATG GCC AGT CGG CCG AGG ATC CCT AG
CAT CGT CGT CCA CAT TAC AGA CGT CGG TAC CGG TCA GCC GGC TCC TAG GGA TC
Val Ala Ala Gly Val Met Ser Ala Gln Ala Met Ala>
 a   a   a   a   a  LAMB4 a   a   a   a   a   a >

FIG. 3E
```

```
         10         20         30         40         50         60         70         80
CTTGTCACCCAGGTGGCACCCGAGTGGTGCACTCTCTGCTCACTGCAACCTCGGCCTGGTTCGAGTGATTCTCCTACCTCA
         90        100        110        120        130        140        150        170
GCCTACTGAGTAGCTGGGATTACACGCGTGCAGCACTATGCCCGGTTAATTTTGTATTTTGGTAGAGATGAGGTTTCACCATG
        180        190        200        210        220        230        240        250
TTGACCAGCTGCTCTGGAACTCCTCACCTCAAGTGATCATCCACCTGCCTCCCAGCCTCCCAAGTGCTGGGATTAGAGGTGTGGGCAC
        260        270        280        290        300        310        320        330        340
AGTGCCTGGCCTGTAGTAGTTGAATATTATTAATCTACAAGTTGCGATTACGCAAGCCCTAGATATAGGGTCCCCAAAC
        350        360        370        380        390        400        410        420
TTCTAGAACAAGGGCTTCCCCACAATCCTGGCAGGCAAGCCTCCCCCTGGGGTTCCCAACTTCTTTCCCCACTGAAGTTTTACCC
                                                  intron ⌐
                430        440        450        460         470          480         490
CCTTCTCTAATCCCAGCCCTCCCTCTTTCGTCTC CAG GTG CTC CGA GAG (ATG) CTC CCT CTC CCC TCA TGC
                                     Q   V   L   R   E   M    L   P   L   P   S   C
    500        510        520        530        540        550
TCC CTC CCC ATC CTC CTC CTT TTC CTC CTC CCC AGT GTG CCA ATT GAG TCC CAA CCC CCA CCC
 S   L   P   I   L   L   L   F   L   L   P   S   V   P   I   E   S   Q   P   P   P
 *        *        *        *        *        *
```

FIG. 11A

```
560         570         580         590         600         610         620
 *           *           *           *           *           *           *
TCA ACA TTG CCC CCT TTT CTG GCC CCT GAG TGG GAC CTT CTC TCC CCC CGA GTA GTC CTG TCT
 S   T   L   P   P   F   L   A   P   E   W   D   L   L   S   P   R   V   V   L   S>

630         640         650         660         670         680
             *           *           *           *           *           *
AGG GGT GCC CCT GCT GGG CCC CCT CTG CTC TTC CTG CTG GAG GCT GGG GCC TTT CGG GAG TCA
 R   G   A   P   A   G   P   P   L   L   F   L   L   E   A   G   A   F   R   E   S>

690         700         710         720         730         740
             *           *           *           *           *           *
GCA GGT GCC CCG GCC AAC CGC AGC CGG CGT GGG GTG AGC GAA ACT GCA CCA GCG AGT CGT CGG
 A   G   A   P   A   N   R   S   R   R   G   V   S   E   T   A   P   A   S   R   R>

750         760         770         780         790         800         810
 *           *           *           *           *           *           *
GGT GAG CTG GCT GTG TGC GAT GCA GTC AGT GGC TGG GTG ACA GAC CGC CGG ACC GCT GTG GAC
 G   E   L   A   V   C   D   A   V   S   G   W   V   T   D   R   R   T   A   V   D>

820         830         840         850         860         870
             *           *           *           *           *           *
TTG CGT GGG CGC GAG GTG GAG GTG TTG GGC GAG GTG CCT GCA GCT GGC GGC AGT CCC CTC CGC
 L   R   G   R   E   V   E   V   L   G   E   V   P   A   A   G   G   S   P   L   R>
```

FIG. 11B

```
                 880            890           900           910           920           930
                  *              *             *             *             *             *
CAG TAC TTC TTT GAA ACC CGC TGC AAG GCT GAT AAC GCT GAG GAA GGT GGC CCG GGG GCA GGT
 Q   Y   F   F   E   T   R   C   K   A   D   N   A   E   E   G   G   P   G   A   G>

940           950           960           970           980           990           1000
         *             *             *             *             *             *             *
GGA GGG GGC TGC CGG GGA GTG GAC AGG AGG CAC TGG GTA TCT GAG TGC AAG GCC AAG CAG TCC
 G   G   G   C   R   G   V   D   R   R   H   W   V   S   E   C   K   A   K   Q   S>

1010          1020          1030          1040          1050          1060
         *             *             *             *             *             *
TAT GTG CGG GCA TTG ACC GCT GAT GCC CAG GGC CGT GTG GGC TGG CGA ATT GAC
 Y   V   R   A   L   T   A   D   A   Q   G   R   V   G   W   R   I   D>

1070          1080          1090          1100          1110          1120          1130
         *             *             *             *             *             *             *
ACT GCC TGC GTC TGC ACA CTC CTC AGC CGG ACT GGC CGG GCC TGA GAC CCA TGC CCA GGA AAT AAC AGA G
 T   A   C   V   C   T   L   L   S   R   T   G   R   A>
       1140          1150          1160          1170          1180          1190          1200          1210
         *             *             *             *             *             *             *             *
CTG GAT GCT CAG AGA CCT CAG GAT GGC CCA GTT TGG GAA CTC ATC AAA TAA TCA CAA ATC ACA AAT CAC AAT
      1220          1230          1240          1250          1260          1270          1280          1290          1300
         *             *             *             *             *             *             *             *             *
CTC TGA TTT GAG CTC CAA TCT CTG CAG GAT GGG GTG AAA CCA CAT GGG GTT TTT GGA GGT TTT TGA AAT AGG AGT TCT CCT GGA GCA ACT
      1310          1320          1330          1340          1350          1360          1370          1380
         *             *             *             *             *             *             *             *
TCA GGG TAA TAA TGA TGA TGA TAA TAA TAG CCA CTA TTA CTG ATG TGT TTA CTG TTT TCT TAT CCC TAA TAC ATA ACT CCT
      1390          1400
         *             *
CAG ATC AAC TCT CAT G
```

FIG. 11C

MODIFIED LAMβ SIGNAL SEQUENCE AND PROCESSES FOR PRODUCING RECOMBINANT NEUROTROPHINS

This application is a continuation-in-part of application Ser. No. 07/715,185, filed Jun. 12, 1991, now abandoned which is incorporated by reference in its entirety.

TABLE OF CONTENTS

1. Introduction
2. Background Of The Invention
3. Summary Of The Invention
4. Description Of The Drawings
5. Detailed Description Of The Invention
6. Example: Production and Recovery of Recombinant hNGF From E. Coli
7. Example: Production and Recovery of Recombinant hBDNF and hBDNFmyc From E. Coli
    7.1. Signal Sequences Based On LamB
    7.2. Production And Recovery Of Recombinant hBDNFmyc
    7.3. Production And Recovery Of Recombinant hBDNF
8. Example: Production And Recovery Of Recombinant hNT-3
9. Example: Production And Recovery Of Recombinant hNT-4 from E. Coli
    9.1. Construction Of pRG173
    9.2 Purification of Human NT-4 Expressed In E. Coli RFJ26/pRG173
    9.3. Preparation Of Enriched Motor Neuron Cultures
    9.4. Results
    9.5. Discussion
10. Deposit Of Microorganisms

1. INTRODUCTION

This invention relates to the fields of neurobiology, molecular biology and protein biochemistry and, in particular, to neurotrophins and methods of producing and recovering them.

2. BACKGROUND OF THE INVENTION

The neurotrophins are a group of proteins involved in the functioning of the nervous system. They stimulate the growth of nerve cells and, during embryonic development, support their survival. To date, researchers have identified four neurotrophins: nerve growth factor (NGF) (Ullrich et al., 1983, Nature 303:821-825), brain derived neurotrophic factor (BDNF) (Leibrock et al., 1989, Nature 341:149-152), neurotrophic factor 3 (NT-3) (Maisonpierre et al., 1990, Science 247:1446-1451) and neurotrophin-4 (Hallbook et al, 1991, Neuron 6:845-858). Nerve growth factor is essential for the development and survival of the peripheral and sympathetic nervous system and the cholinergic neurons of the brain. It is currently being tested for use in Alzheimer's disease. BDNF promotes the survival of sensory neurons in the central nervous system and shows promise as a therapy for Parkinson's disease. NT-3 and NT-4 are newly discovered and their biological role is now being investigated. Like NGF, NT-3 seems to act on sensory and sympathetic neurons.

Native human NGF has three subunits: α, β and γ. Only the β subunit has neurotrophic activity. β-NGF is produced as a pre-pro-protein which is secreted from the cell and processed into the mature form. The pre-pro-peptide contains 187 amino acid residues. During processing, the pre- and the pro-sequences are removed, as are two amino acid residues at the C-terminus. This yields a mature protein of 118 amino acid residues. The mature protein has six cysteine residues that form three disulfide bonds. The protein also contains many basic amino acids resulting in a positive charge at neutral pH.

Structurally, the neurotrophins form a family, apparently having evolved from a common ancestral gene. (Hyman et al., 1991, WO 91/03568.) For example, the amino acid sequence of the β polypeptide of human NGF (hNGF) is 90% homologous to mouse NGF and bovine NGF; and the three human neurotrophins, hNGF, hBDNF and hNT-3, share 60% homology at the amino acid level. The six cysteine residues are conserved in all known neurotrophins, implying that the disulfide bonds are important for function.

Natural sources of neurotrophins are limited. The mouse submaxillary gland is rich in NGF but isolation is difficult and the quantities recovered, small (Hyman et al., 1991, WO 91/03568). della Valle et al. (EP 0 333 574, 1989) have reported the isolation of small amounts of hNGF from human placenta by chromatographic fractionation.

Therefore, researchers have turned to molecular genetics to provide a ready source of biologically active neurotrophins. DNA sequences encoding NGF, BDNF and NT-3 have all been isolated (Ullrich et al., Nature 303:821-825; Hyman et al., WO 91/03568; Hohn et al., WO 91/03569; and Kaisho et al., FEBS Letters 266:187-191). Researchers have transformed animal and non-animal hosts with these sequences in order to express the neurotrophins.

Kanaya et al. (1989, Gene 83:65-74) fused a DNA sequence encoding mature hNGF to one encoding the yeast α-mating factor pre-pro sequence. Upon expression, the culture supernatant contained a protein recognized by α-hNGF antibodies. However, the partially purified protein exhibited low neurotrophic activity. Furthermore, the level of expression was low. Kanaya et al. stated that these results may have been due either to the failure of the yeast system to remove the two extra C-terminal amino acid residues during maturation or to a problem with folding the hNGF protein.

Chan et al. (EP 0 370 171, 1990) produced mature hNGF in insect cells. They fused a gene for pre-pro-hNGF to the polyhedrin promoter and leader sequence of baculoviral DNA. They reported the production of 6 μg/ml hNGF, but did not physically characterize the product.

Researchers have also expressed human NGF, BDNF and NT-3 in mammalian expression systems. Bruce and Heinrich (1989, Neurobiology of Aging 10:89-94) expressed a DNA sequence encoding the complete precursor for hNGF in COS cells and detected hNGF dimer in the conditioned medium. However, they could not determine the efficiency at which pre-pro-hNGF was converted to mature hNGF. Kakinuma et al. (EP 0 414 151, 1991) expressed active hNGF in CHO cells. Hyman et al. (WO 91/03568, 1991) expressed hBDNF in CHO cells. Nakahama et al. (EP 0 386 752, 1990) and Hohn et al. (WO 91/03569, 1991) expressed hNT-3 in COS cells.

Mammalian systems provide the most natural environment for the production of mammalian proteins. However, the production of large quantities of proteins in these systems is very expensive. Therefore, there is a need to develop systems that are both less expensive and more productive. One such system is E. coli.

Researchers have attempted to produce neurotrophins in E. coli, but without significant success. Gray and Ullrich (EP 0 121 338, 1984) constructed an expression vector encoding N-methionyl-hNGF and expressed the gene in E. coli. They reported identification of hNGF by immunodetection on Western blot, but they did not isolate the protein or demonstrate biological activity.

Hu and Neet (1988, Gene: 57–65) attempted to express mouse NGF in E. coli. They cloned a DNA sequence encoding a mature mouse NGF in which they replaced serine, the N-terminal amino acid in the native protein, with methionine. They inserted the DNA sequence into a plasmid having a temperature inducible lambda $P_L$ promoter. This system expresses other heterologous proteins at rates of 10%–25% total cellular protein. They expressed the gene and isolated NGF by ammonium sulfate precipitation followed by dialysis against acetate buffer. However, as tested by bioassay, this system yielded only 0.0005% to 0.1% NGF. The authors speculated that the highly inconsistent and low yields were due to toxicity of NGF to the cells, instability or translational inefficiency of the mRNA, or mismatched disulfide bonds in the refolded, oxidized protein.

Iwai et al. (1986, Chem. Pharm. Bull. 34:4724–4730) reported synthesis of a gene encoding hNGF with codons preferred in E. coli. They expressed the gene directly as N-methionyl-hNGF or as a fusion protein with human growth hormone. Direct expression was only one-fourth as efficient as expression of the fusion protein. They examined the proteins by SDS-PAGE, but did not otherwise isolate them.

Dicou et al. (1989, J. Neurosci. Res. 22:13–19) expressed mouse pre-pro-NGF and a fragment of hNGF as fusion proteins with β-galactosidase and found that the addition of protease inhibitors improved yield.

In summary, previous attempts to express neurotrophins in E. coli have resulted in cell death, low levels of protein accumulation, and expression of protein with virtually no biological activity.

3. SUMMARY OF THE INVENTION

This invention provides processes for producing and recovering biologically active recombinant neurotrophins from non-animal host cells. Processes for producing recombinant neurotrophins comprise the step of culturing a host cell transformed with a recombinant DNA molecule comprising an expression control sequence operatively linked to a DNA sequence encoding a neurotrophin. When the neurotrophins are expressed directly into the cytoplasm, the host cells preferably are protease-deficient mutants and, according to the best mode of which we are aware, heat shock regulatory gene mutants. In bacterial hosts, the neurotrophin gene is preferably under the control of a controllable promoter and expression is preferably un-induced or repressed until the cells reach late log phase. The neurotrophins may be also secreted from the cell during production by providing a DNA sequence encoding a signal peptide upstream of the DNA sequence encoding the neurotrophin.

Processes for recovering biologically active recombinant neurotrophins produced by host cell cultures comprise the step of solubilizing the neurotrophin in a solution comprising a strong denaturing agent, the solution being essentially free of reducing agents. According to one embodiment of the invention the solution further comprises a protease inhibitor in an amount effective to inhibit degradation of the neurotrophin by proteases. Other embodiments of the invention further comprise some or all of the following steps: exchanging the strong denaturing agent for a weak denaturing agent; adjusting the solution to comprise a basic amino acid or equivalent at a concentration effective to maintain solubility of the neurotrophin in a non-denaturing environment; purifying the neurotrophin from other molecules in the solution; removing the weak denaturing agent; and completing the purification in the absence of the denaturing agent.

In a further embodiment of the invention, the neurotrophin molecule expressed in E. coli and recovered in a biologically active form is neurotrophin-4. In a preferred embodiment of the invention directed to expression of biologically active NT-4 in E. coli, the NT-4 is encoded by a nucleic acid molecule comprising a sequence substantially as set forth for hNT-4 in FIGS. 11A–11C (SEQ ID NO: 22) or may comprise a sequence that is at least about seventy percent homologous to such a sequence.

4. DESCRIPTION OF THE DRAWINGS

FIG. 1 is a schematic representation of plasmid pRPN133. The solid line represents pBR322-derived DNA sequences with the origin of replication (ORI) and the β-lactamase gene (ampicillin resistance) (Ap) indicated. Distinctive features of the plasmid are indicated by boxed regions with arrowheads indicating the direction of transcription or replication. PL indicates the lambda $P_L$ promoter. rbs1 is the wild type promoter and ribosome binding site of phage T7 φ1.1. The hNGF gene encodes a mature polypeptide in which the second amino acid residue, serine is replaced by threonine. cI857 indicates the heat inactivatable λ repressor gene.

Figure 2A:
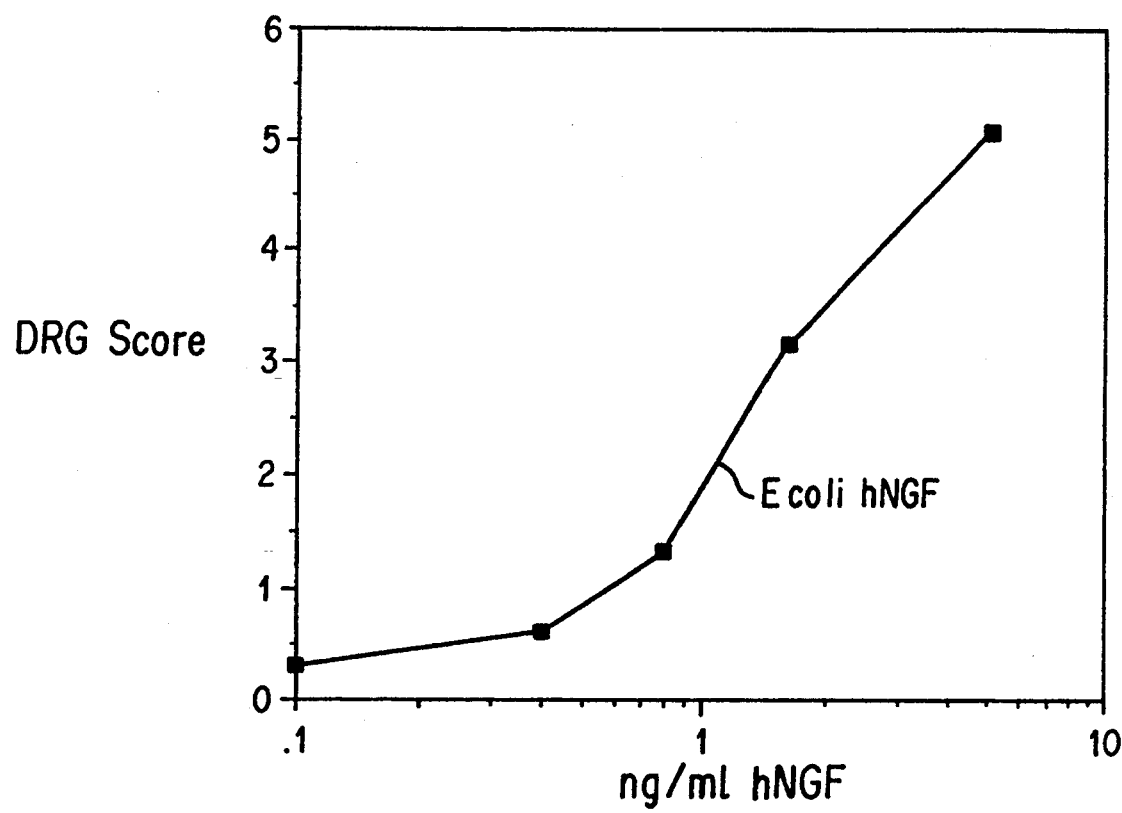
Figure 2B:
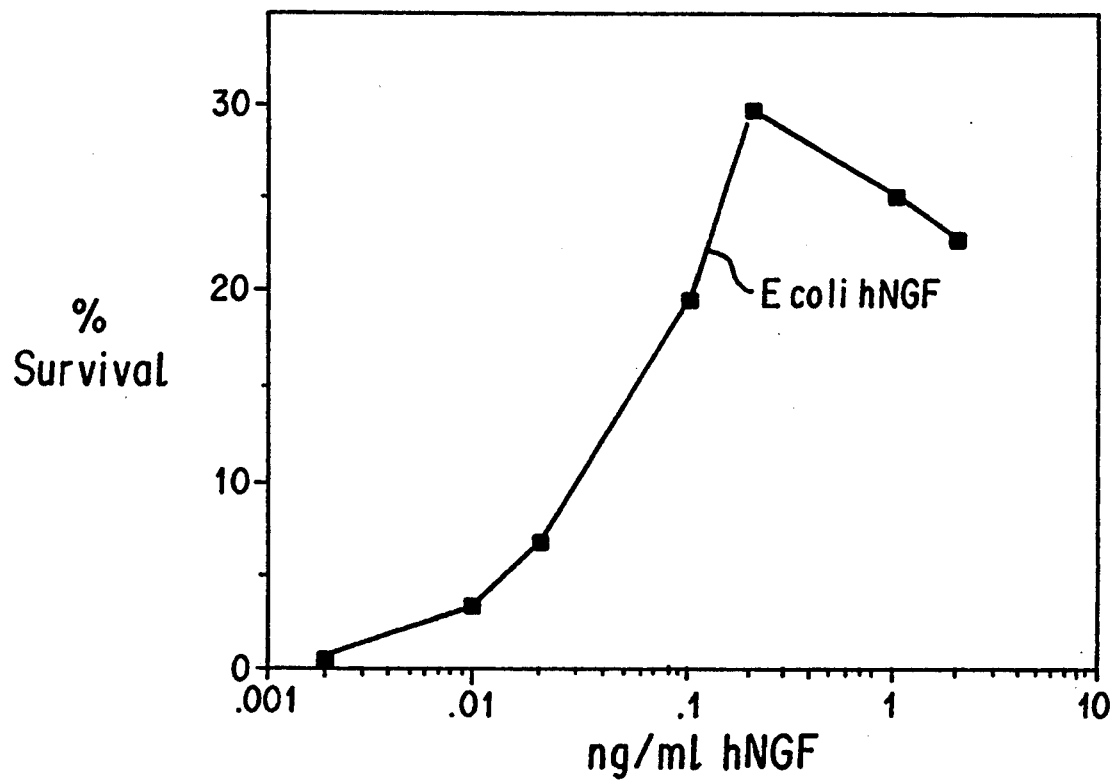

FIGS. 2A–B show dose-response curves to recombinant human NGF produced in E. coli by (FIG. 2A) E8 chick embryo dorsal root ganglia (DRG) explants and (FIG. 2B) dissociated E8 DRG.

FIGS. 3A–E depict the nucleotide and amino acid sequences of wild type Lamb (FIG. 3A, SEQ ID NO: 1) and the synthetic Lamb signal sequences, LamB1 (FIG. 3B, SEQ ID NO: 2), LamB2 (FIG. 3C, SEQ ID NO: 3), LamB3 (FIG. 3D, SEQ ID NO: 4) and LamB4 (FIG. 3E, SEQ ID NO: 5).

Figure 4:
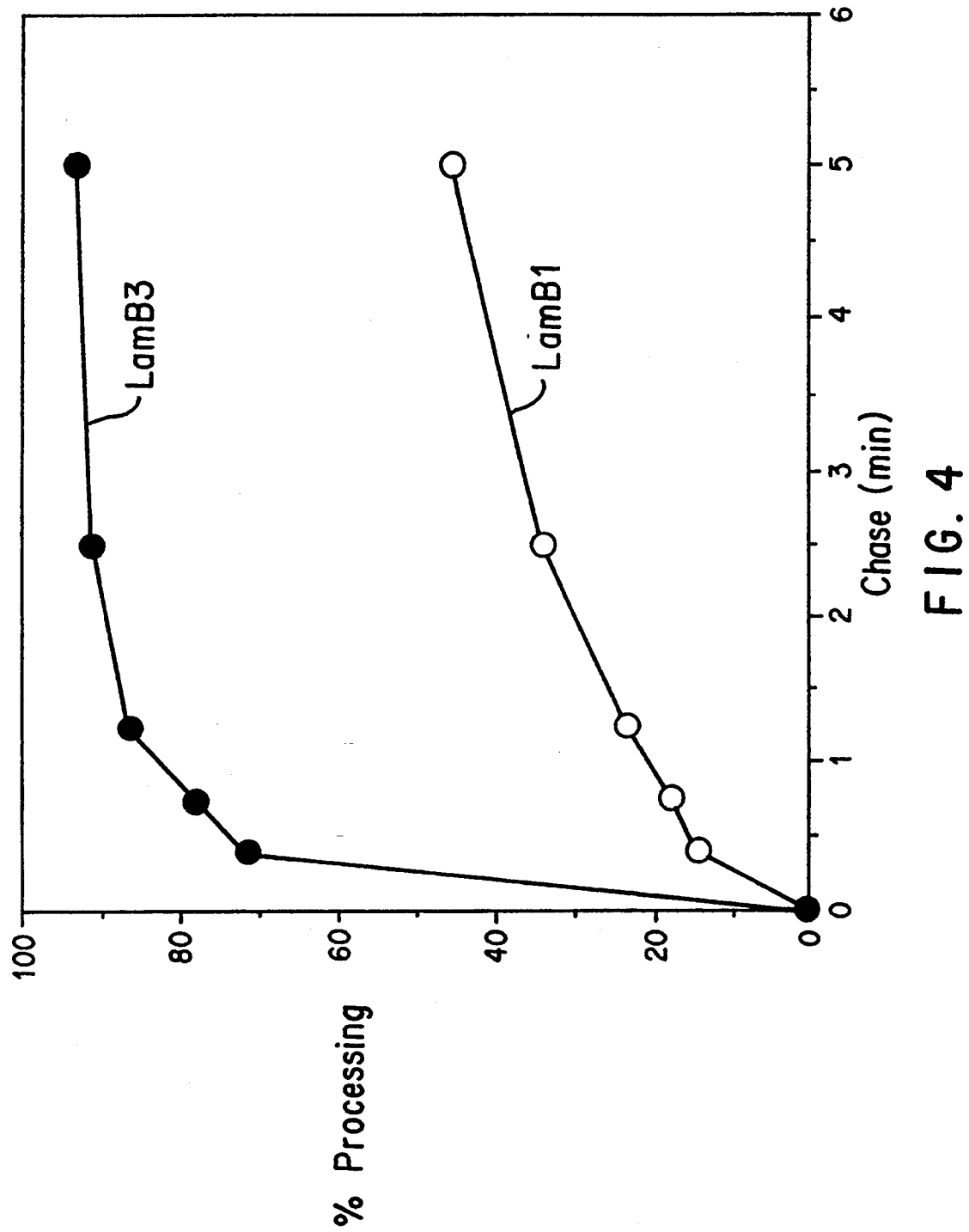

FIG. 4 depicts the signal sequence processing kinetics of the modified LamB signal sequences, LamB1 and LamB3. We cultured strain BL21/DE3 containing the appropriate LamB-hBDNF plasmid. In this strain, the gene encoding T7 RNA polymerase has been inserted in the chromosome and is under the transcriptional control of the lac promoter (Studier and Moffatt, J. Mol. Biol. 189:113–30). Addition of IPTG to the growing cells for 10 minutes allows synthesis of T7 RNA polymerase. Subsequent addition of rifampicin to 0.2 mg/ml blocks transcription by E. coli RNA polymerase but allows transcription by T7 RNA polymerase. This results in selective transcription of the LamB—hBDNF gene which is placed immediately downstream from the T7 late φ1.1 promoter and ribosome binding site of rbs2. Cells were pulsed with $^{35}$S-methionine for 30 seconds and then chased with an excess of cold methionine. The cultures were sampled at the indicated times after chase and the labelled proteins were analyzed by SDS-15% PAGE and fluorography. Processing was determined by densitometric scanning of the precursor and mature forms of LamB-hBDNF.

Figure 5:
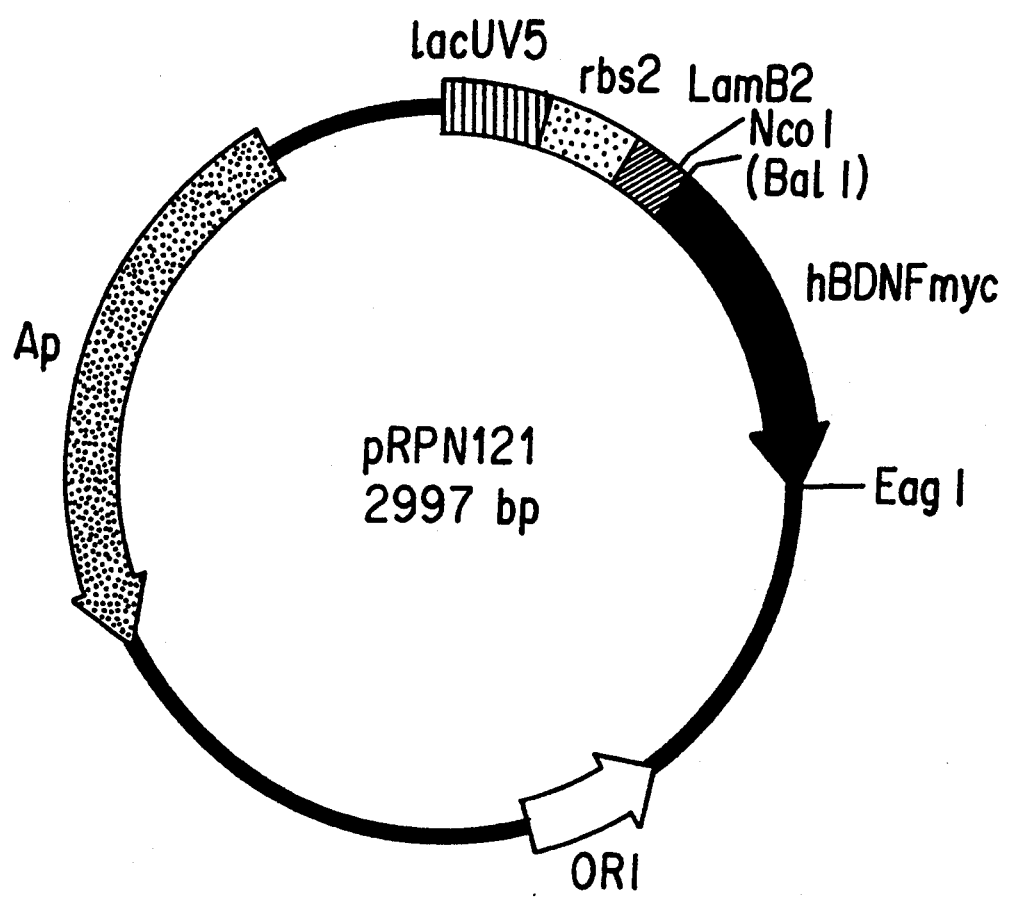

FIG. 5 is a schematic representation of pRPN121. The solid line represents pBR322-derived DNA sequences with the origin of replication (ORI) and the β-lactamase gene (Ap) indicated. Distinctive features of the plasmid are indicated by boxed regions with arrowheads indicating the direction of transcription or replication (ORI). LacUV5 is the promoter. rbs2 indicates the T7 φ1.1 promoter and the T7 φ1.1 ribosome binding site with minor nucleotide substitutions from the wild type designed to create convenient restriction sites. LamB2 is the signal sequence. hBDNFmyc is the structural gene.

Figure 6:
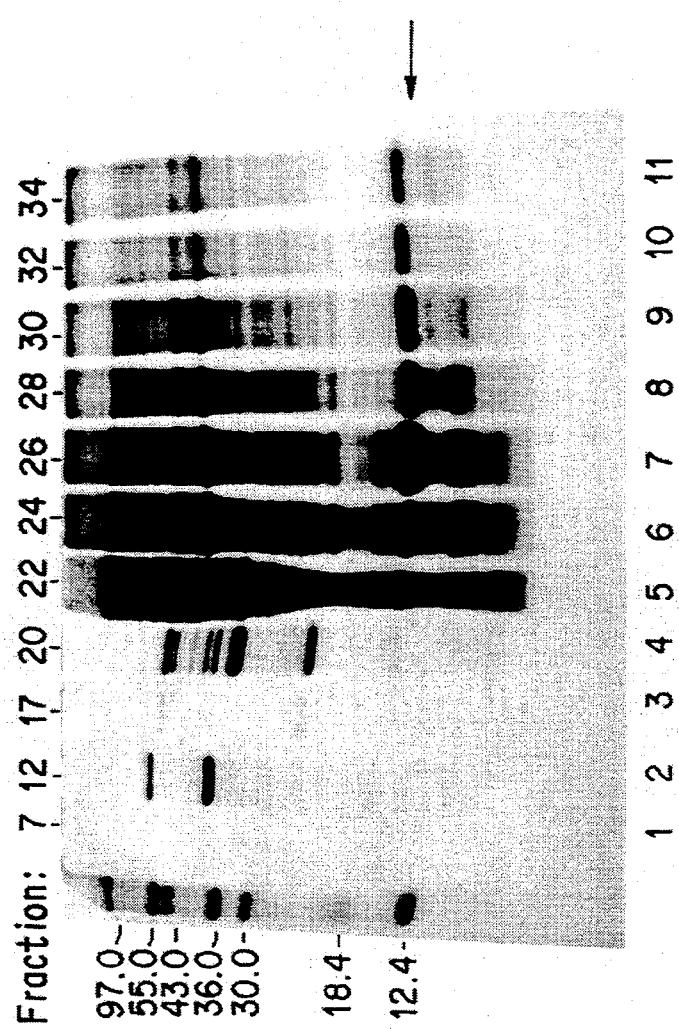

FIG. 6 depicts a protein profile of Fast S-SEPHAROSE® 1 fractionation of hBDNFmyc. W3110 I9F−/pRPN121 extract after DEAE chromatography was fractionated as described on a 1.6 cm×6.5 cm Fast S-SEPHAROSE® column in 7M urea, 50 mM histidine, pH 5.0, 1 mM EDTA. Fractions as indicated were analyzed by SDS-15% PAGE and proteins visualized by Coomassie stain. Fractions 26–30 were pooled.

Figure 7:
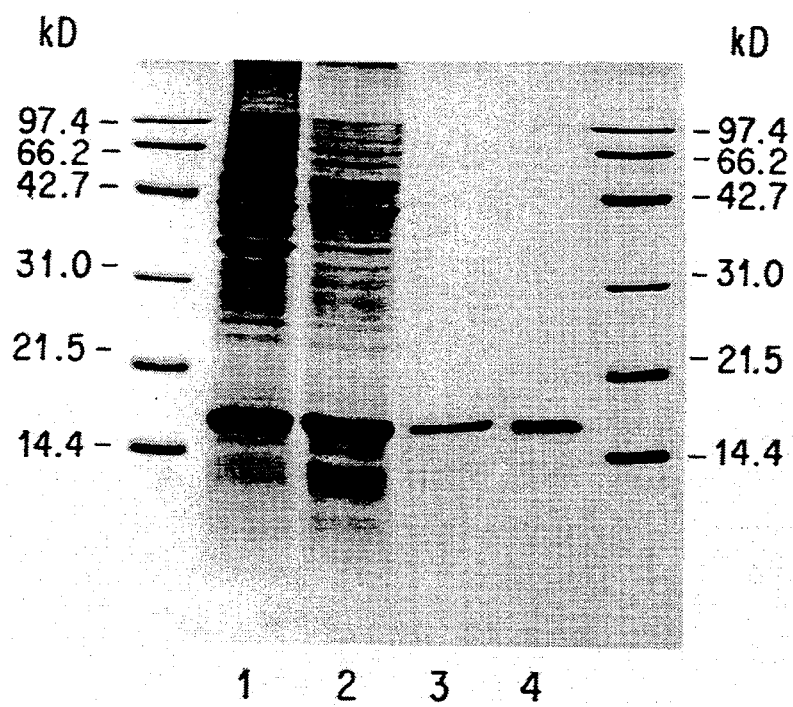

FIG. 7 is a summary of the purification procedure. Strain W3110 I9F/pRPN121 was grown, induced, and extracted as described above. Pooled column fractions were analyzed by SDS-PAGE on a 15% acrylamide gel and stained with Coomassie Blue. Lane 1, DEAE; lane 2, Fast S-SEPHAROSE® 1; lane 3, Fast S-SEPHAROSE® 2; lane 4, C4 reverse phase HPLC. Molecular weight standards are indicated.

Figure 8:
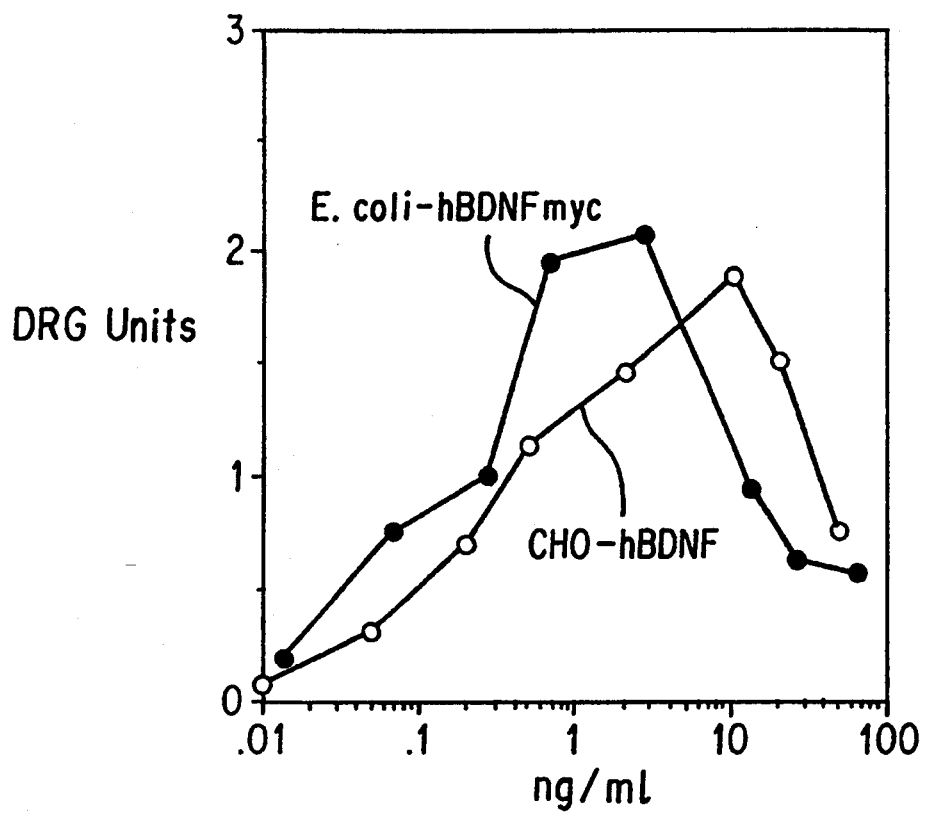

FIG. 8 depicts a dose response curve for purified hBDNFmyc stimulation of E8 chicken embryo DRG neurite outgrowth. The hBDNFmyc activity is compared with recombinant hBDNF purified from a Chinese hamster ovary cell line. Both proteins were purified to greater than 95% by C4 reverse phase HPLC.

Figure 9:
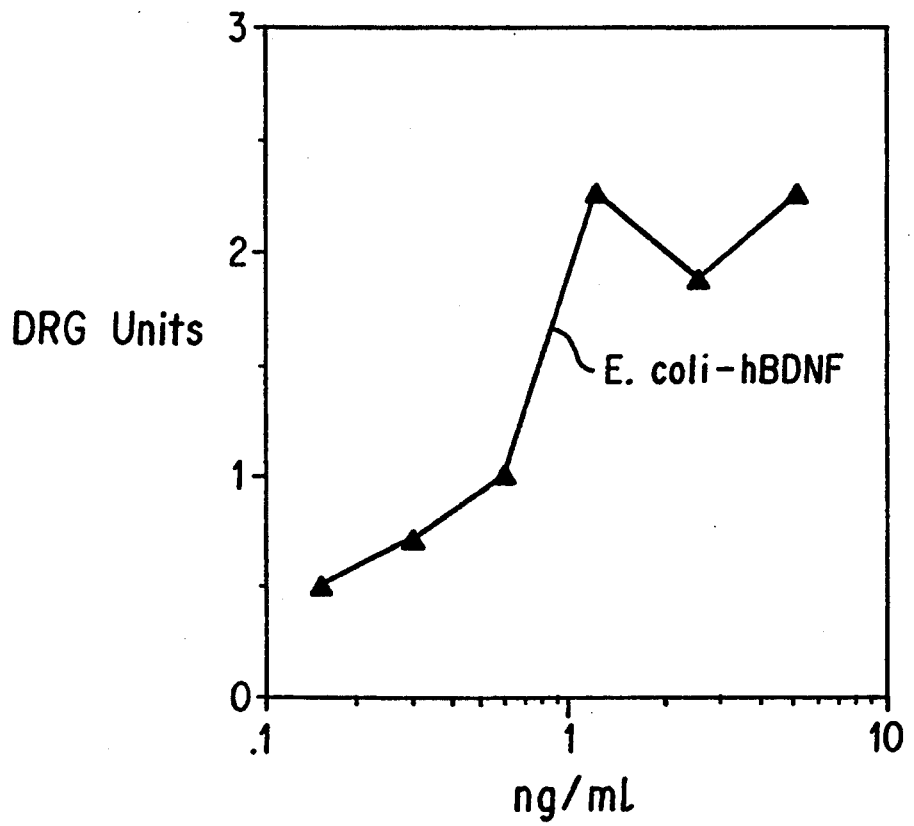

FIG. 9 depicts a dose response curve for the stimulation of E8 chicken embryo DRG neurite outgrowth by recombinant hBDNF purified from E. coli. The hBDNF was purified to greater than 95% by C4 reverse phase HPLC.

Figure 10:
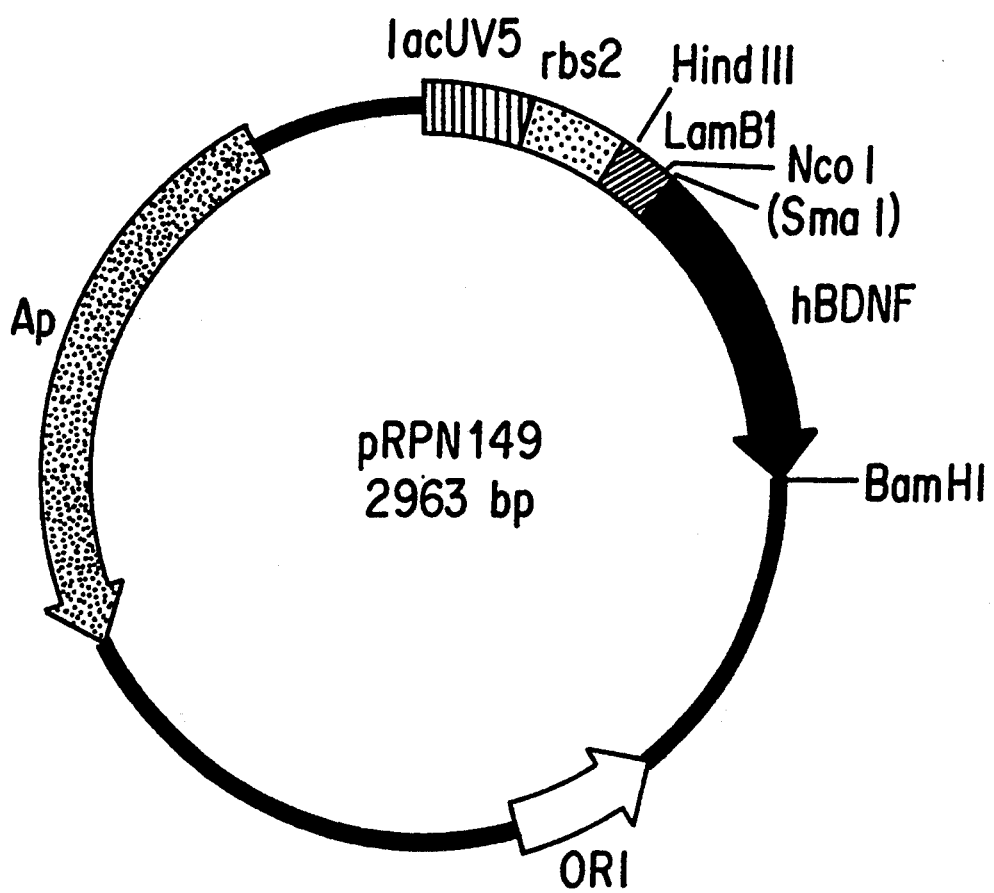

FIG. 10 is a schematic representation of pRPN149. The solid line represents pBR322-derived DNA sequences with the origin of replication (ORI) and the β-lactamase gene (Ap) indicated. Distinctive features of the plasmid are indicated by boxed regions with arrowheads indicating the direction of transcription or replication (ORI). LacUV5 is the promoter. rbs2 indicates the T7 φ1.1 promoter and the T7 φ1.1 ribosome binding site with minor nucleotide substitutions from the wild type designed to create convenient restriction sites. LamB1 is the signal sequence. hBDNF is the structural gene.

FIGS. 11A–11C is the DNA sequence of a portion of the isolated human genomic phage clone 7-2 encoding human NT-4 (SEQ ID NO: 22; ATCC Accession No: 75070. The predicted hNT-4 protein encoded by the genomic clone 7-2 is represented by the one-letter symbols for amino acids (SEQ ID NO: 23). The boxed region represents the predicted cleavage site of the hNT-4 preprotein. Arrows indicate conserved residues in the presequence. The underlined region (N-R-S) represents a consensus sequence for N-glycosylation. The circled region represents the initiating methionine. The splice acceptor site is located at base pair 461–462 (AG), representing the 3′-end of the intron.

Figure 12:
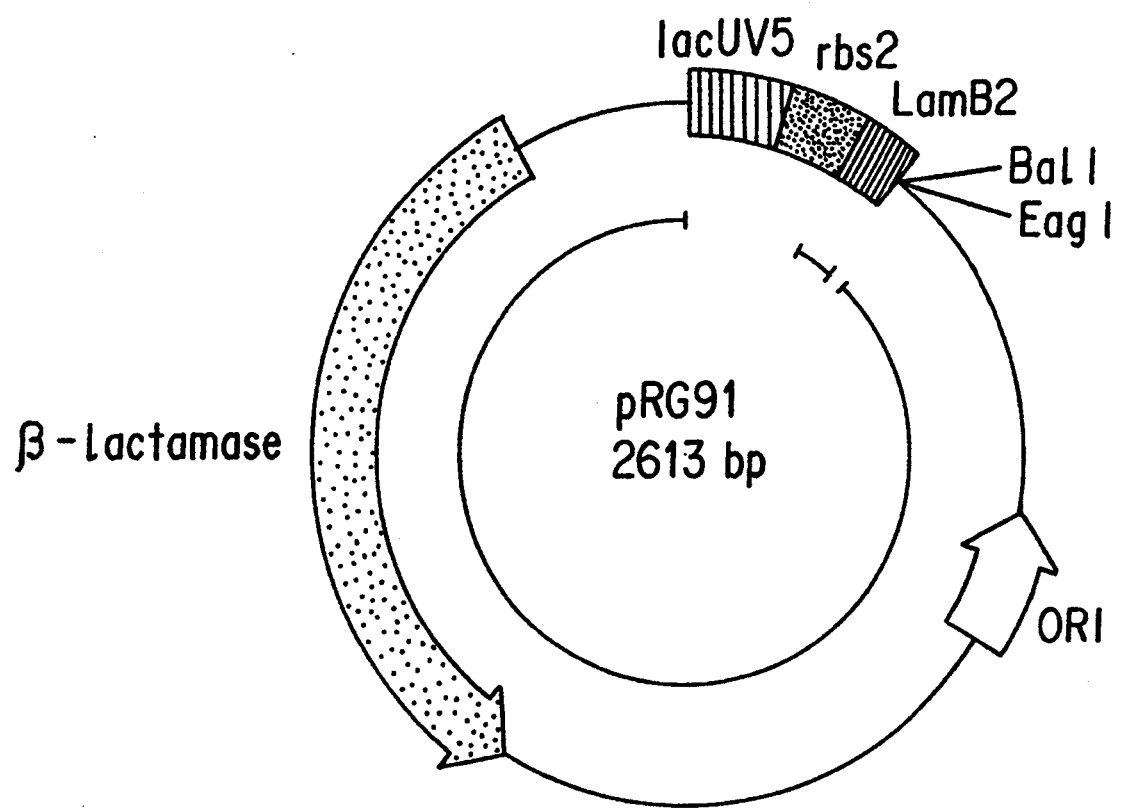

FIG. 12 is a schematic representation of pRG91. The solid line represents pBR322-derived DNA sequences with the origin of replication (ORI) and the β-lactamase gene indicated. Distinctive features of the vector are shown by boxed regions. LacUV5 is the promoter. rbs2 is the phage T7 φ1.1 promoter and the T7 φ1.1 ribosome binding site. LamB2 is the signal sequence.

Plasmid pRG91 (Regeneron Pharmaceuticals) is a pBR322-based vector designated for the expression of recombinant proteins and their secretion into the periplasmic space of Escherichia coli. The vector consists of the strong, regulated, lacUV5 promoter followed by the phage T7 φ1.1 promoter and ribosome binding site inserted between the EcoRI and NruI restriction sites in pBR322. These control elements direct the expression of the LamB2 signal sequence to which recombinant protein gene sequences may be fused. The DNA sequences between the unique NruI and PvuII restriction sites were deleted, resulting in increased plasmid copy number. This plasmid confers ampicillin (Ap) resistance.

Figure 13:
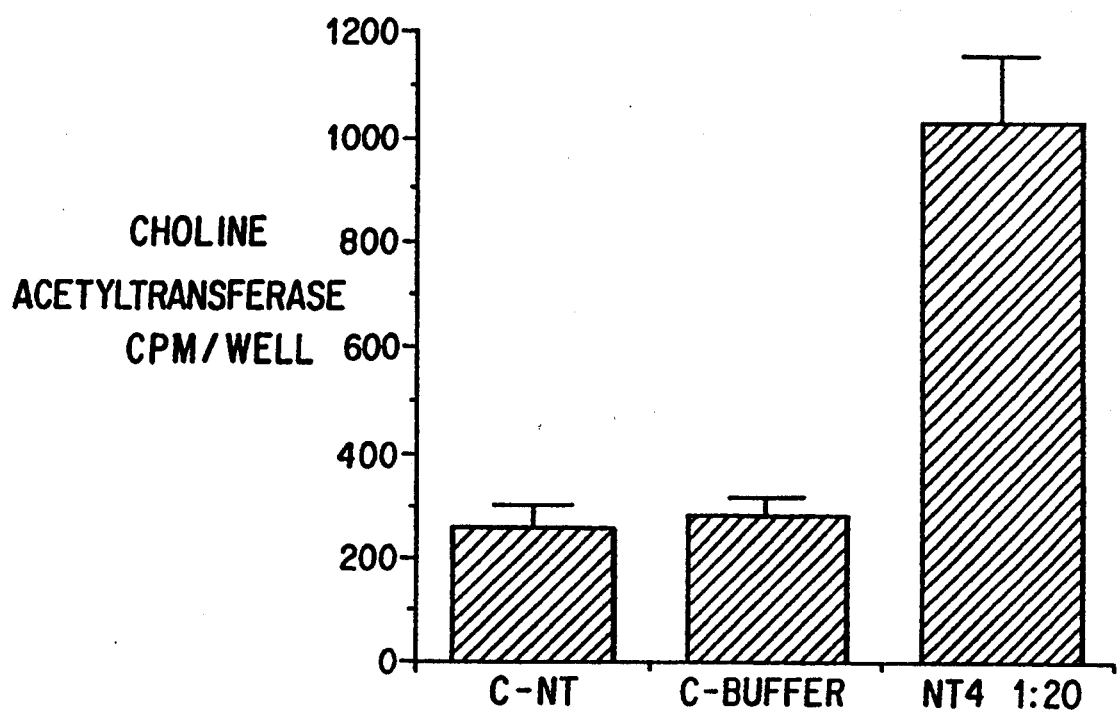

FIG. 13 depicts the effect of hNT-4 on CAT activity. Treatment of motor neuron enriched cultures with a partially purified extract from an induced culture of strain RFJ26 containing plasmid pRG173 resulted in a 3.6-fold (at 1:20 dilution) increase in CAT activity after 48 hours as compared to untreated (C-NT) and buffer (C-buffer) controls. The E. coli extract was passed through a Sepharose-S column as disclosed infra prior to treatment of motor neuron enriched cultures.

5. DETAILED DESCRIPTION OF THE INVENTION

As used herein, the term "neurotrophin" refers to any naturally occurring member of the neurotrophin family. This includes naturally occurring proteins sharing amino acid sequence homology with any known neurotrophin and conserving the six characteristic cysteine residues. (Some of these proteins may fall structurally into the neurotrophin family, yet may exhibit biological activity other than neurotrophic activity.) The term "neurotrophin" also refers to engineered neurotrophins whose amino acid sequences are derived from or patterned after the naturally occurring neurotrophins. For example, it includes chimeric neurotrophins comprising amino acid sequences from different neurotrophins (e.g., NGF and NT-3) or from the same neurotrophin of different species (e.g., hBNDF and pig BDNF); neurotrophins whose genetic sequences have point substitutions, addition or deletion mutations; neurotrophins derived from the pre-pro-sequence (e.g., neurotrophins having the two carboxy-terminal amino acid residues encoded by the codons immediately preceding the stop codon of the native gene ("full length neurotrophin")); and includes fragments of a neurotrophin which exhibit neurotrophic activity (e.g., those whose first six amino acids are altered or deleted). These examples are descriptive and not meant to limit the definition.

This invention provides processes for producing and recovering biologically active recombinant neurotrophins. It further provides the purified, homogeneous, recombinant neurotrophins made by these processes. A recombinant protein, as used in this specification, is a protein expressed from a recombinant DNA molecule in a host cell transformed with it. A recombinant DNA molecule is a hybrid molecule comprising DNA sequences from different sources that have been joined together. Sambrook et al. (1989, Molecular Cloning: A Laboratory Manuel, Cold Spring Harbor Laboratory Press, Cold Spring Harbor) describes many conventional techniques for recombinant DNA technology.

According to this invention, producing recombinant neurotrophins involves culturing a non-animal host cell transformed with a recombinant DNA molecule having an expression control sequence operatively linked to a DNA sequence encoding a neurotrophin. An expression control sequence is operatively linked to a DNA sequence encoding a polypeptide when the expression control sequence directs and promotes the transcription and translation of the DNA sequence. Culturing a transformed host cell involves incubating the cell in culture conditions appropriate for the growth of the cell and the expression of the DNA sequence.

DNA sequences encoding neurotrophins are available from several sources. The literature discloses DNA sequences for the four known human neurotrophins (i.e., hNGF (Gray et al., EP 0 121 338, 1984), hBDNF (Hyman et al., WO 91/03568), hNT-3 (Hohn et al., WO 91/03569) and Xenopus NT-4 (Hallbook, et al., 1991, Neuron 6:845–858) and for many non-human neurotrophins. Preferably, one refers to these sequences for direction to construct oligonucleotide primers suitable for PCR amplification. Genomic libraries are suitable sources of DNA for PCR templates. Also useful are cDNA libraries of cells known to express neurotrophin mRNA. For example, cDNA libraries of human fetal brain mRNA contain sequences for hBDNF. One may also screen cDNA and genomic libraries using any of the methods known to the art to identify and isolate DNA sequences encoding neurotrophins. Alternatively, one may construct synthetic or semi-synthetic genes using conventional DNA synthesizers. Undoubtedly, researchers will discover DNA sequences encoding new neurotrophins. The methods of this invention will be useful for producing and recovering these neurotrophins, as well.

In specific, the invention relates generally to production of NT-4 or a derivative or fragment thereof by growing a recombinant bacterium containing a nucleic acid encoding NT-4 or derivative or fragment under conditions such that the NT-4 or derivative or fragment thereof is expressed by the bacterium, and recovering the produced NT-4 or NT-4 derivative or fragment. In a preferred embodiment, the NT-4 is human NT-4. In another embodiment, an NT-4 derivative which is a chimeric or fusion protein is produced. In a most preferred embodiment, the produced NT-4, or NT-4 derivative or fragment is biologically active, i.e., capable of exhibiting one or more of the known functional activities of NT-4, as assayed by any methods known in the art or taught herein (e.g., in vitro assays of the ability to promote outgrowth in E8 DRG explants, the ability to stimulate CAT activity in purified motor neuron cultures; see Section 9, infra).

In a specific embodiment of the invention, sequences encoding human NT-4 are expressed in an E. coli expression system and a purification scheme as disclosed infra is used to produce useful amounts of human NT-4. The nucleic acid encoding human NT-4 which is thus expressed can be that contained in nucleic acid pRG173 (ATCC Accession Number 75131) or HG7-2 (ATCC Accession Number 75070) or shown in FIGS. 11A–C (SEQ ID NO: 22), or isolated by any methods known in the art, as follows: Mixtures of 5' and 3' oligonucleotides representing all possible codons corresponding to known NT-4 sequences or to conserved amino acid sequences from known neurotrophins are utilized as primers in the polymerase chain reaction (PCR). Primary and secondary PCR amplification reactions of human (or other mammalian) cDNA or genomic libraries result in the isolation of a PCR product that can be utilized as $^{32}$P-labelled probes to isolate a full length cDNA or genomic clone encoding NT-4. The term "human neurotrophin-4" as used herein should be understood as meaning any human homologue of the Xenopus NT-4 (Hallbook, et al., 1991, Neuron 6:845–858), including a distinct yet homologous (e.g., at least about seventy percent homology) neurotrophin molecule.

The literature discloses a variety of expression control sequences useful for expressing DNA sequences in transformed non-animal hosts. These include, among others, in bacteria, the lac system, the trp system, the TAC system, the TRC system, the lambda $P_L$ promoter, the T7 late promoters, and the control regions of the fd coat protein; and in yeast, the phosphoglycerate kinase promoter, the Gal 4 promoter, the His promoter, the alcohol dehydrogenase promoter, the alkaline phosphatase promoter and the α-mating factor promoter. Controllable expression control sequences are preferable and, among these, a temperature inducible lambda $P_L$ promoter, the lacUV5 promoter and the T7 $\phi$1.1 promoter are most preferable for expression in E. coli.

The literature also discloses a variety of expression vector/host systems suitable for bacterial and fungal hosts, including plasmids, bacteriophages, cosmids and derivatives of them. Examples of these systems are, for bacteria, col F1, pCR1, pBR322, pMB9, RP4, phage lambda, M13 and filamentous viruses; and, for yeast, 2 μ. Preferred plasmids in bacteria are stable in the host cell and present at medium copy numbers of 20–200 copies per cell. We used plasmids derived from pBR322, such as those described by Panayotatos (1987, Engineering an Efficient Expression System, in: Plasmids-A Practical Approach, ed. Herdy, K., IRL Press, Oxford/Washington, D.C.). In particular, we prefer plasmids of the RPN class, developed by Regeneron Pharmaceuticals, Inc. and described more fully below.

The art is also familiar with many non-animal hosts useful to express heterologous proteins, including E. coli, Bacillus, Streptomyces, Saccharomyces and Pichia pastoris. We prefer E. coli.

Culturing transformed host cells results in the expression of neurotrophins. We have found that neurotrophins expressed in bacteria are subject to degradation by intracellular proteases, especially those induced as part of the "heat shock" response to foreign proteins (Goff et al., 1984, Proc. Natl. Acad. Sci. USA 81:6647–6651). Therefore, we prefer to use protease-deficient mutants as host cells.

The expression of the heat shock genes is regulated by heat shock regulatory genes, such as the htpR gene of E. coli. Mutants of the HtpR gene are deficient in expression of heat shock protease genes, as well as other genes that contribute to the heat shock response. We have found that expressing recombinant neurotrophins in heat shock regulatory gene mutants, especially htpR$^-$ mutants, significantly improves yield. HtpR$^-$ lon$^-$ double mutants are particularly useful. We prefer the E. coli strain LC137, an htpR$^{ts}$ lon$^-$ mutant. This strain is available from Prof. Alfred Goldberg, Harvard University. U.S. Pat. No. 4,758,512 (Goldberg et al.) describes other suitable strains. Another preferred E. coli strain is RFJ26.

Neurotrophins are toxic to bacterial cells that express them. Therefore, in order to maximize yield, we prefer to induce neurotrophin expression only in dense bacterial cultures, for example, cultures in late log phase. We have used an inducible system based on the lambda $P_L$ promoter and the cI857 temperature sensitive repressor. We typically induce production of neurotrophins by shifting growth temperature to 42° C. for 30 minutes and continuing incubation for 3–20 hours at 38°–42° C.

Inducing expression for more than 16 hours in actively growing cells eventually causes cell death.

The inability of E. coli to accumulate neurotrophins may be the result of one or more properties of the neurotrophin gene or protein. The structure of the neurotrophin mRNA, particularly the structure proximal to the translation start point, may prevent efficient translation. Alternatively, the neurotrophin may prevent its own synthesis by interacting directly with its mRNA, or it may interact directly or indirectly with some component of the DNA replication/transcription/translation machinery of E. coli.

According to another embodiment of our invention, we secrete the neurotrophin into the periplasmic space of E. coli rather than express it intracellularly. We accomplish this by fusing a signal sequence to a mature neurotrophin. A signal sequence gene fused to the 5' end of the neurotrophin gene may provide a nucleotide sequence proximal to the translation startpoint that is more conducive to efficient translation, thus resulting in higher levels of neurotrophin accumulation. In addition, sequestering the neurotrophin in the periplasmic space prevents it from interfering with any cytosolic component necessary for protein synthesis. It also protects it from attack by cytosolic proteases. It is also possible that the secretion of a mature neurotrophin into the periplasmic space may provide an environment more conducive to the proper folding of the protein.

A signal sequence is provided by constructing a recombinant DNA molecule in which the DNA sequence encoding the neurotrophin comprises, from 5' to 3' a fused gene encoding a signal or leader sequence appropriate to the host cell which is in-frame with a DNA sequence for the neurotrophin. The literature describes several signal sequences useful in such constructions. For example, LamB, OmpA and PhoA are useful in E. coli. (Denèfle et al., 1985, Gene 85:499-510; Wong et al., 1988, Gene 68:193-203). We prefer LamB and, in particular, modified LamB signal sequences that improve the translational efficiency of the LamB mRNA. We constructed genes for modified LamB signal sequences in the following manner. We made degenerate substitutions to the third nucleotide of several codons of LamB, replacing G or C with A or T. These substitutions do not change the amino acid sequence of the LamB signal peptide, but do decrease the potential number of hydrogen bonds in any secondary structure. This reduces the stability of possible secondary structures involving this region of LamB mRNA. We also introduced codon changes based on codon usage models, to more nearly approximate codons used most frequently by E. coli.

We also modified the LamB signal sequence to improve efficiency of processing of the Lamb precursor protein into mature protein. Native LamB has a hydrophobic core of 10 amino acid residues. Mutational analysis of several E. coli signal sequences suggests that the length of the hydrophobic core region can have a strong effect on signal sequence activity. We have found that increasing the length of the hydrophobic region by the addition of up to ten hydrophobic amino acid residues improves the efficiency of processing LamB fusion precursor polypeptides. Fewer than six is preferable and four is most preferable. The choice of hydrophobic amino acids added is not critical, nor is the precise location at which they are added to the hydrophobic core region. However, we prefer to add the tetra-peptide Leu-Ala-Val-Leu ("LAVL") (SEQ ID NO: 6) at a convenient restriction site near the N-terminal end of the hydrophobic region. We describe particular genes for modified Lamb signal sequences in Example 7.

In accordance with our invention, the recombinant neurotrophins are released from the culture of host cells by harvesting the cells, lysing them, centrifuging the lysate and collecting the lysate pellet. One typically harvests the cells by centrifugation. To inhibit degradation of the neurotrophin after harvesting the cells, one preferably resuspends them in 50 mM EDTA. Then we either use the cells directly or freeze them for later use. The art is familiar with many techniques to lyse cells including enzymatic (e.g., lysozyme), chemical (e.g., alkali, SDS) and mechanical (e.g., French press, hydrodynamic shear). Mechanical means are preferred because there is less risk of harm to the neurotrophins. We prefer to lyse the cells by passing them through a French press or a STANSTED® cell disrupter at 10,000 psi. We obtain the lysate pellet by centrifugation, at about 15,000×g.

This invention further provides processes for recovering the recombinant neurotrophins produced in cell cultures. These processes overcome the problems associated with conventional methods of recovering recombinant proteins that have been applied to neurotrophins.

Native neurotrophins are soluble in neutral buffers. However, recombinant neurotrophins from E. coli behave as insoluble proteins. Recombinant neurotrophins have been detected in the cytosolic fraction and, when exported, have been recovered from the periplasmic space using standard techniques such as osmotic shock, spheroplasting, or freeze-thaw (Bochner et al., U.S Pat. No. 4,680,262). However, they are isolable only as a small fraction of the total neurotrophins in the cell.

Many mammalian proteins expressed in bacteria are insoluble. Produced in a foreign ionic environment, they do not fold correctly and expose normally hidden hydrophobic regions. Consequently, the proteins form aggregates and precipitate as inclusion bodies. The literature suggests that the cysteine residues of these proteins are at least partially reduced or mismatched (Tsuji et al., 1987, Biochemistry 26:3129-3134).

The literature describes standard techniques for purifying recombinant proteins from inclusion bodies (see, e.g., Builder et al., U.S. Pat. No. 4,620,948; Hershenson et al., U.S. Pat. No. 4,961,969; and Hung et al., U.S. Pat. No. 4,734,362). These techniques involve dissolving the protein in a solution comprising a strong denaturant and a reducing agent. After exchanging the strong denaturant for a weak denaturant, the proteins are renatured in a neutral solution and oxidized to form the correct disulfide bonds.

The majority of the recombinant neurotrophin produced by these methods is biologically inactive. We believe that this is due, in part, to the complexity of the neurotrophins' tertiary structure. After denaturing the protein and reducing the sulfhydryl groups, the polypeptide does not refold into the proper configuration for the correct disulfide bonding. Furthermore, our results suggest that recombinant neurotrophins are present in aggregates that are not typical inclusion bodies.

We have discovered a process to recover biologically active recombinant neurotrophins from the insoluble host cell fraction. Essentially, the process involves solubilizing the neurotrophin in a strong denaturing agent while maintaining the correct oxidation state of the protein by avoiding the use of reducing agents. Reducing the disulfide bonds during purification destroys the activity of purified neurotrophin polypeptides. Because the literature (e.g., Tsuji et al. 1987, Biochemistry 26:3129–3134) teaches that insoluble recombinant proteins in inclusion bodies should have incorrectly formed or reduced disulfide bonds, this is an unexpected result.

To further recover the neurotrophins, the strong denaturing agent is replaced with a weaker one. We have also discovered, however, that the addition of a basic amino acid, such as histidine, or its equivalent, helps keep the neurotrophin soluble during the renaturation process that accompanies the removal of the weak denaturant (Prior et al., 1990, WO 90/06764).

These discoveries suggest to us a new model for the behavior of recombinant neurotrophins. We believe that the majority of the recombinant neurotrophin polypeptides produced by the host cell fold properly and form the correct disulfide bonds. Furthermore, since neurotrophins have a high pH and are positively charged at neutral pH, we believe that they form associations with negatively charged molecules in the cell, for example DNA, RNA and other proteins. Consequently they become insoluble at neutral pH. Basic amino acids help to dissociate them.

More specifically, our process for recovering recombinant neurotrophins produced by a host cell culture comprises the step of denaturing the neurotrophin by dissolving it in a solution comprising a strong denaturing agent which solution is also essentially free of reducing agents. Denaturing agents as used herein refer to compounds which, in aqueous solution, reversibly unfold dissolved proteins by at least partially eliminating tertiary and secondary structure through the disruption of hydrogen bonds or alteration of the thermodynamic surroundings of the protein. Strong denaturing solutions include guanidinium salts (e.g., guanidinium hydrochloride) and alkali metal thiocyanates (e.g., sodium thiocyanate) at concentrations of 4M–9M, and urea at 7M–9M. The preferred denaturing solutions are 7M–9M guanidinium HCl. Preferred conditions are pH 7.0–pH 9.0 and room temperature. Most preferred is 8M guanidinium HCl, pH 8.0.

One must also maintain the correct oxidation state of the sulfur atoms in the cysteine residues during this step or risk losing the ability to recover any biologically active neurotrophins. Therefore, the solution must be essentially free of reducing agents. A solution essentially free of reducing agents is one in which a protein's disulfide bonds are maintained. Addition of even small amounts of disulfide reducing agents, such as β-mercaptoethanol or dithiothreitol, during the practice of this invention will destroy the activity of the purified neurotrophin.

Recombinant neurotrophins apparently are subject to degradation by metalloproteinases. Therefore, preferably, one recovers neurotrophins in solutions comprising metalloproteinase inhibitors. We prefer heavy metal chelators, such as EDTA. The concentration of EDTA may range from a minimum of at least 1 mM to a maximum of about 200 mM. Concentrations of 5 mM–80 mM are preferable and 50 mM is most preferable. After chelated heavy metal ions have been dialyzed from the solution, EDTA may be reduced or eliminated. Langley et al., 1990, EP 0 398 753, describes peptides useful as metalloproteinase inhibitors.

The recovery process may also comprise one or more of the following steps. After solubilizing the neurotrophin, one exchanges the strong denaturing agent in the solution for a weak denaturing agent. Weak denaturing solutions include urea at 4M–9M and, preferably, 6M–8M, pH 7.0–pH 9.0, at room temperature. The most preferable weak denaturing solution is 7M urea, 50 mM Tris-HCl, 10 mM NaCl, 5 mM EDTA, pH 8.0. Dialysis is the preferred method of exchange. If the strong denaturing agent is 7.0M–9.0M urea, the weak denaturing agent of this step is preferably urea of lower concentration.

In order to renature the neurotrophin, one removes the weak denaturing agent from the solution. Dialysis or diafiltration against a non-denaturing solution is the preferred method of removal. We prefer 0M to 1M NaCl as a non-denaturing solution.

Another step in the recovery process is purifying the recombinant neurotrophin from other contaminants in the solution. Any of the typical protein isolation techniques known to the art may be used. We prefer a three step isolation involving cation exchange on S-SEPHAROSE®, anion exchange on DEAE-SEPHAROSE® and reverse phase high pressure liquid chromatography (HPLC). The isolation step can begin at any stage after solubilization of the neurotrophin and may continue through the denaturing agent exchange and removal steps. Preferably, we begin purification at the urea phase, because this agent does not interfere with ion exchange chromatography and because partial purification made the neurotrophin easier to dissolve in the non-denaturing solution.

We have found that unless the neurotrophin is relatively purified it will precipitate out of the solution when one removes the weak denaturing agent. Solubility depends upon degree of purity of the neurotrophin as well as the character of the other contaminants in solution. For example, negatively charged molecules such as DNA will interfere with solubility of even very pure neurotrophin. Therefore, we maintain the solubility of the neurotrophin in the non-denaturing solution by adjusting the solution to comprise a basic amino acid or an equivalent, such as indole acetic acid. The concentration of this species should be effective to maintain the neurotrophin in solution. Solutions of basic amino acids include histidine, lysine and arginine or their salts at concentrations above 10 mM. Histidine in concentrations of 20 mM–500 mM is useful. We most prefer histidine in concentrations of 20 mM–100 mM. If the neurotrophin in the denaturing solution has been sufficiently purified before removal of the denaturant, this step may be eliminated.

Results indicate that our method produces uniform neurotrophin molecules, consistently having the same N-terminal amino acid. In contrast we have found that expression of neurotrophins in the mammalian CHO cell system produces a mixture of neurotrophin molecules with varying N-terminal amino acids. Therefore, the recombinant neurotrophins produced by our process appear to be unique.

The processes of this invention are also useful for recovering other proteins having biochemical properties similar to the neurotrophins. That is, the processes are useful for recovering proteins that fold correctly in bacteria and form the proper disulfide bonds, but, once denatured and reduced in conventional recovery techniques, are very difficult to renature with proper disulfide bonds. This includes proteins with pH greater than about 9.0 and having at least two disulfide bonds. (Candidate molecules include secretory leukocyte protease inhibitor (Miller et al., 1989, J. Bacteriology 171:2166-2172) and full length recombinant CD4 (Fisher et al., 1989 WO 89101940).)

As described in an example section infra, the present invention discloses the expression of biologically active human neurotrophin-4. The human NT-4 DNA sequence was subcloned into the DNA plasmid vector pRG91, resulting in pRG173. This hNT-4 containing plasmid was transformed into E. coli strain RFJ26, and methods described in the instant specification were utilized to recover biologically active NT-4 from the culture system. However, applicants are not to be limited to such a specific embodiment. For example, any nucleic acid sequence substantially homologous to the region of HG7-2 encoding human NT-4 can be utilized to construct any number of DNA plasmid expression vectors as described throughout the specification or known to the skilled artisan, which in turn can be utilized to transform any number of E. coli bacterial strains in order to produce useful amounts of biologically active NT-4.

In order that this invention may be better understood, the following examples are set forth. These examples are for the purposes of illustration only, and are not to be construed as limiting the scope of the invention in any manner.

6. EXAMPLE: PRODUCTION AND RECOVERY OF RECOMBINANT hNGF FROM E. COLI

A DNA sequence carrying the mature human NGF (hNGF) gene was amplified from human genomic DNA using known human NGF sequences (Nancy Ip; Regeneron Pharmaceuticals, Inc.) by PCR amplification. We used the oligo-deoxynucleotide primers PAN-20 (5'-AAGCGGTCGA CATCTCATCC AATCTT-CCAT AGAGGTGAAT TCTCAGTA-3') (SEQ ID NO: 7) and EVD-3 (5'-GGCAGGCGGC CGTCATCTCA CAGCCTTCCT GCTG-3') (SEQ ID NO: 8). These primers were designed to incorporate a SalI restriction site at the 5' end and an EagI restriction site at the 3' end of the human NGF gene. In order to incorporate a SalI site at the 5' end with PAN-20, it was necessary to change the second amino acid from the amino terminal sequence of the mature hNGF protein from serine to the structurally similar amino acid threonine. In view of the limited sequence identity of the three known neurotrophins in their eight N-terminal amino acids, such conservative amino acid changes should not affect activity. Furthermore, the identity of the amino acid residue in this position is not preserved in NGF molecules from other species (Ibanez et al., 1990, EMBO J. 9:1477-1483). In addition, PAN20 was designed so as to lower the G+C content of this region of the NGF gene in a manner that does not affect the sequence of the resulting protein.

The amplified DNA fragment was digested with the restriction endonucleases SalI and EagI and ligated between the SalI and EagI sites of pRPN50, (Regeneron Pharmaceuticals, Inc.), resulting in plasmid pRPN102. pRPN50 is derived from expression plasmid pNKS97 (Panayotatos, 1987, Engineering an Efficient Expression System, In: Plasmids-A Practical Approach, ed. Herdy, K., IRL Press, Oxford/Washington, D.C.) by the insertion of the lambda $P_L$ promoter at the promotor insertion site.

The cI857 lambda $P_L$ repressor gene was incorporated into pRPN102 to facilitate repression at 30° C. and to allow derepression by heat shock at 42° C. This DNA sequence was PCR amplified using the primers EVD-26 (5'-CCATTATCGC GACCAGAGGT-3') (SEQ ID NO: 9) and EVD-27 (5'-TCTTGCTCGC GAGTTAT-CAG CTATGCG-3')(SEQ ID NO: 10) that generate a NruI restriction site at each end. This 821 bp fragment extends 70 bp upstream from the cI857 coding sequence in a region that contains the PRM constitutive promoter as well as 38 bp beyond the cI857 termination codon. The PCR amplified cI857 fragment was digested with NruI and ligated into the NruI site of pRPN102. Candidates from this ligation were screened to find a plasmid with the cI857 insert that had the same transcriptional direction as the hNGF gene, resulting in plasmid pRPN133 (FIG. 1). Plasmid pRPN133 has been deposited with the ATCC and has been assigned Accession No: 75029.

We transformed the E. coli htpR$^{ts}$ Rts lon$^-$ mutant strain, LC137, with RPN133 to yield pRPN133/LC137.

In a 2 liter flask, 400 mL of LB medium supplemented with 100 mg/L ampicillin was inoculated with pRPN133/LC137 and incubated at 28° C. with shaking. At late logarithmic growth phase ($OD_{590}=1.0-2.0$ under these conditions), hNGF synthesis was induced by adding to the overnight culture 400 mL of LB media preheated to 55° C. and continuing incubation with shaking at 42° C. for 5 hours.

Cells were harvested by centrifugation and the cell pellets stored at −20° C. Cell pellets (1.0-2.5 g) were thawed, resuspended in 20.0 mL buffer A (100 mM Tris-HCl, 50 mM EDTA, pH 8.0), passed through a STANSTED ® cell disrupter at 10,000 psi, and centrifuged at 23,000×g for 15 minutes at 4° C. The pellet was washed twice with 10.0 mL of 2M guanidinium-HCl, 5 mM EDTA, pH 8.0.

To solubilize the recombinant hNGF, we resuspended the pellet in 40 mL of 8M guanidinium-HCl, 5 mM EDTA, pH 8.0 using a Potter homogenizer. Then we centrifuged the suspension at 23,000×g for 15 minutes.

The supernatant was dialyzed against 2 liters buffer B (7 M urea, 100 mM histidine, 0.1 mM EDTA, pH 6.0) with two buffer changes at 25° C. for 20 hours. The dialysate was centrifuged at 23,000×g for 15 minutes at 4° C.

The supernatant was applied to an S-SEPHAROSE ® column (2.5 cm×6.0 cm d×h) equilibrated in buffer B and washed to baseline absorbance at 280 nm with the same buffer. Proteins were eluted with a gradient of 300 mL of 0.0M−1.0M NaCl in buffer B. Fractions containing hNGF were pooled.

The pooled fractions were dialysed against 100-fold excess volume buffer C (7M urea, 50 mM Tris-HCl, 0.1 mM EDTA, pH 8.5) at 25° C. for 20 hours.

The dialysate was applied to a DEAE-SEPHAROSE column (2.5×7.5 cm d×h) equilibrated in buffer C at a flow rate of 2.0 mL per minute. The flow-through fractions containing the hNGF were pooled and dialyzed twice against 40 volumes of 100 mM histidine, 0.1 mM EDTA, pH 6.0 at 4° C. overnight. The dialysate was centrifuged at 23,000×g for 15 minutes at 4° C. The dialysate was then applied to a TOYOPEARL CM 6505 ® (weak cation exchange) column (1.0×5.0 cm) equilibrated with 100 mM histidine, 0.1 mM EDTA, pH 6.0 and eluted with a 0.0M to 1.0M NaCl gradient. Fractions containing the hNGF were pooled and filtered through MILLIPORE GV ® filter and stored at 4° C. The amino terminal sequence of the purified protein was confirmed by direct sequencing.

The biological activity of the purified protein was tested for neurite outgrowth in E8 explanted and dissociated dorsal root ganglia (FIG. 2A and 2B) (Lindsay et al., 1985, Dev. Biol. 112:319–328). By this criteria the recombinant hNGF purified from E. coli by this method was found to be as active as NGF purified from mouse salivary gland.

7. EXAMPLE: PRODUCTION AND RECOVERY OF RECOMBINANT hBDNF and hBDNFmyc FROM E. COLI

7.1. SIGNAL SEQUENCES BASED ON LAMB

We constructed signal sequences based on LamB to facilitate both the synthesis and secretion of neurotrophins in E. coli. The Lamb signal sequence (FIG. 3A, SEQ ID NO: 1) is a naturally occurring E. coli signal sequence which was selected for the construction of a series of secretion vectors based on the pRPN series of expression vectors developed at Regeneron Pharmaceuticals, Inc. Secretion vectors were constructed by cloning synthetic DNA fragments encoding the Lamb signal sequence into pRPNO9 or pRPN16. These plasmids derive from expression vector pNKS97 (Panayotatos, 1987, Engineering an Efficient Expression System, In: Plasmids-A Practical Approach, ed. Herdy, K., IRL Press, Oxford/Washington, D.C.) into which have been inserted a lacUV5 promoter. LamB was inserted into the structural gene insert site such that expression of Lamb is under control of the lacUV5 or T7 φ1.1 promoter.

The synthetic DNA fragment, LamB1 (FIG. 3B, SEQ ID NO: 2), encodes 25 amino acids identical to the wildtype LamB signal sequence. However, we altered the nucleotide sequence relative to the wild type nucleotide sequence for the purpose of constructing unique restriction enzyme sites and for the maximization of translation efficiency. LamB1 also has seven degenerate nucleotide substitutions replacing C or G with A or T. This reduces the stability of possible secondary structure of mRNA. LamB1 also has several new restriction sites.

We also created LamB2 (FIG. 3C, SEQ ID NO: 3) as a modification of LamB1. To make LamB2 we made nucleotide changes to the 3' end of LamB1 by PCR amplification. These changes introduced an EagI restriction site which facilitates the cloning of blunt end DNA fragments.

The fusion of mature hBDNF to LamB1 results in efficient synthesis of the fusion protein in E. coli. The authenticity of the synthesized product was confirmed by selective synthesis in a DNA-dependent coupled transcription-translation cell-free protein synthesis system, by the selective synthesis of the product using a T7 RNA polymerase expression system in E. coli, and by the synthesis of the product with a C-terminal myc tag allowing for identification of the chimera with a myc-specific monoclonal antibody. Either one of these fusion proteins synthesized in E. coli was processed to mature hBDNF as evidenced by its mobility on SDS-PAGE. The level of expression obtained with LamB1 or LamB2 results in accumulation of hBDNF from about 1% to 10% of total cell protein.

We modified LamB1 to increase the efficiency of processing. Four amino acids (Leu-Ala-Val-Leu, or LAVL) were inserted into the NheI site of LamB1 to yield LamB3 (FIG. 3D, SEQ ID NO: 4). The same insertion was made in LamB2 to yield LamB4 (FIG. 3E, SEQ ID NO: 5). This insertion results in extension of the hydrophobic core region of LamB1 and LamB2 from 10 to 14 amino acids. It results in a 5-fold increase in the rate of processing of the hBDNF fusion protein into mature hBDNF (FIG. 4).

LamB3- and LamB4-hBDNF molecules that are exported into the periplasm are processed into mature hBDNF more rapidly than wild type Lamb fusions. However, fewer molecules are exported, so the net amount of mature hBDNF in this case is not increased. In any case the increased translocation efficiency of LamB3 and LamB4 should result in improved yields of other proteins.

The LamB1 signal sequence fragment was constructed as two complementary synthetic oligonucleotides (LamB80, 5'-ATGATCACAC TCCGCTAGCT GTAGCAGTAG CAGCAGGTGT AATGTCT-GCA CAGGCCATGG CCCGGGATCC-3' (SEQ ID NO: 11) and LamB88, 5'-CTAGGGATCC CGGGCCATGG CCTGTGCAGA CATTACACCT GCTGCTACTG CTACAGCTAG CGGAAGCTTA CGCAGTGTGA TCATCATG-3' (SEQ ID NO: 12)), designed so as to generate upon annealing protruding ends corresponding to those of the SpeI and SphI restriction sites. This DNA fragment was ligated into the SphI and SpeI restriction sites of pRPN16 (Regeneron Pharmaceuticals, Inc.) resulting in plasmid pRPN52.

This plasmid was subsequently modified, for the purpose of creating additional restriction sites, by the insertion of a synthetic DNA fragment, consisting of the annealed product of the complementary LamB2A, (5'-CATGGCCAGT CGGCCGAG-3' (SEQ ID NO: 13)) and LamB2B (5'-GATCCTCGGC CGACTGGC-3' (SEQ ID NO:14)) oligonucleotides, between the unique NcoI and BamHI restriction sites in the LamB1 signal sequence in pRPN52. The resulting plasmid, pRPN88, contains the LamB2 signal sequence with unique restriction sites at the signal peptidase recognition sequence to facilitate fusion of the signal sequence to any other DNA sequence. The LamB2 signal sequence in pRPN88 is under transcriptional control of the lacUV5 or the T7 φ1.1 promoter and translational control of the T7 φ1.1 ribosome binding site.

7.2. PRODUCTION AND RECOVERY OF RECOMBINANT hBDNFmyc

Human BDNFmyc is a protein comprising, from N- to C-terminus, mature hBDNF fused to an antigenic "tag." The tag is a peptide having the amino acid sequence EQKLISEEDL (SEQ ID NO: 15) These ten amino acid residues derive from the human c-myc proto-oncogene. Antibodies recognizing this tag are useful for identifying hBDNFmyc in a sample (Evan et al., Mol. Cell. Biol. 5:3610–3616; see also, S. Squinto et al., "Assay Systems for Detecting Neurotrophic Activity," U.S application 07/5321,283, incorporated herein by reference).

To construct a fusion protein comprising the LamB2 signal sequence and the hBDNFmyc protein, the hBDNFmyc DNA sequence was PCR amplified from pCDM8-hBDNFmyc (Regeneron Pharmaceuticals, Inc.) using oligonucleotide primers N8-hBDNF (5'-CCCACTCTGA CCCTGCCCGC CGAGGG-3' (SEQ ID NO: 16)) and C2-hBDNFmyc (5'-GCTATGCGGC CGCTACAGAT CCTCCTC-3' (SEQ ID NO: 17). The amplified DNA fragment was digested with EagI and cloned into the BalI and EagI sites of the LamB2 sequence in pRPN88, resulting in plasmid pRPN98.

One also can produce a DNA sequence encoding hBDNFmyc by fusing a DNA sequence encoding mature hBDNF to one encoding the ten-amino acid myc tag. DNA sequences encoding mature hBDNF are isolated by PCR amplification as described. (Hyman et al., 1991, WO 091/01568.) A double stranded DNA sequence encoding the ten-amino acid myc peptide tag may be chemically synthesized. For the purposes of this Example, the hybrid hBDNFmyc DNA sequence is then provided with BalI and EagI restriction sites at the 5' and 3' ends, respectively.

It should be noted that there are two BalI sites in pRPN88 but the site in the pBR322-derived sequences is about 50 times less sensitive to BalI cleavage than the site in the LamB2 signal sequence due to dcm methylation (New England Biolabs). In pRPN98 the LamB2 signal sequence is fused to the mature part of the hBDNFmyc protein so that cleavage at the signal peptidase recognition sequence should yield hBDNFmyc protein starting at the histidine residue at +1 relative to the pro-protein processing site (Leibrock, 1989, Nature 341:149–152).

The DNA sequences between the unique NruI and PvuII sites in pRPN98 were deleted to remove sequences that control copy number of the plasmid (Twigg and Sherratt, 1980, Nature 283:216–218). The resulting plasmid, pRPN121 (FIG. 5), has a copy number about 3-fold higher than the parental plasmid. Plasmid pRPN 121 has been deposited with the ATCC and been assigned Accession No: 75028.

We transformed E. coli W3110 I$^q$F$^-$ with pRPN121 to produce W3110 I$^q$F$^-$/pRPN121.

In a 2 L flask, 500 ml of LB medium was inoculated with W3110 I$^q$F$^-$/pRPN121 and grown to late log with shaking at 37° C. (OD$_{590}$ approximately 1.0), after which lactose was added to a final concentration of 1% (w/v) and the culture aerated overnight at 37° C. Cells were harvested by centrifugation, washed once in 0.2M Tris-HCl, pH 8.0 and the cell pellet frozen at −70° C.

The cell pellet (approximately 5 g) was thawed and resuspended in 20 mL 0.2M Tris-HCl, pH 8.0, 1 mM CaCl$_2$, and 25 units micrococcal nuclease (Boehringer Mannheim). The cell suspension was passed through a French pressure cell at 8000 psi and then centrifuged at 15,000 rpm for 15 minutes in a SA600 rotor at 4° C. The pellet was resuspended in 30 mL of 0.2 M Tris-HCl, pH 8.0, 10 mM EDTA, 2% Triton X-100 and gently rocked at room temperature for one hour then centrifuged at 15,000 rpm for 15 minutes in a SA600® rotor at 4° C. The pellet was washed twice in 20 mL of 2M guanidinium-HCl. The pellet was resuspended in 10 mL of 8M guanidinium-HCl, 10 mM Tris-HCl, pH 8.5, 10 mM NaCl, 1 mM EDTA using a Potter homogenizer. The extract was brought to 20 mL with the same buffer.

The extract was dialyzed overnight at room temperature against 100×volume 7M urea, 50 mM Tris-HCl, pH 8.5, 10 mM NaCl, 1 mM EDTA.

The dialysate was applied to a DEAE ZETA-PREP® disk (Cuno, Inc., Meriden, Conn.) equilibrated in 7M urea, 50 mM Tris-HCl, pH 8.5, 1 mM EDTA, at a flow rate of 3 mL/minute and washed to baseline with the same buffer.

The flow-through fractions were brought to 50 mM histidine, pH 5.0 then dialyzed overnight at 4° C. against 100×volume 7M urea, 50 mM histidine, pH 5.0, 1 mM EDTA. The dialysate was applied to a 1.6 cm×6.5 cm column of S-SEPHAROSE® equilibrated with 7M urea, 50 mM histidine, pH 5.0, 1 mM EDTA, at a flow rate of 1 mL/minute, and washed to baseline with the same buffer. Proteins were eluted with a NaCl gradient from 0.0M–1.0M in 200 ml. Fractions containing hBDNFmyc were collected (FIG. 6).

Fractions containing hBDNFmyc were dialyzed against 200×volume 50 mM histidine, pH 5.0, 50 mM NaCl, 1 mM EDTA. The dialysate was applied to a 1.6 cm×1.5 cm column of S-SEPHAROSE® equilibrated with 50 mM histidine, pH 5.0, 50 mM NaCl, 1 mM EDTA, at a flow rate of 1 mL/minute and washed to baseline with the same buffer. Proteins were eluted with a NaCl gradient from 0.0M–1.0M in 200 ml. The fractions containing hBDNFmyc were collected and pooled.

The hBDNYmyc in this sample (approximately 85% pure) was applied directly to a 0.45cm×5.0 cm C4 reverse phase column (VYDAC®) and eluted with a gradient of 0–67% acetonitrile in 0.1% trifluoroacetic acid in 80 mL at a flow rate of 0.75 mL/minute. The peak fraction was greater than 95% pure (FIG. 7).

Analysis of the N-terminal amino acid sequence confirmed the purified protein to be authentic hBDNFmyc with a homogeneous N-terminus (Leibrock, 1989, Nature 341:149–152).

The purified hBDNFmyc was biologically active in promoting neurite outgrowth from dorsal root ganglion (DRG) explants and nodose ganglion explants from E8 chicken embryos, as well promoting survival and dendritic outgrowth of dissociated neurons from E8 chicken DRG's (FIG. 8). This activity is comparable to recombinant human BDNF purified from mammalian cell extracts on DRG explant assays. Material assayed corresponds to FIG. 7, lane 4.

7.3. PRODUCTION AND RECOVERY OF RECOMBINANT hBDNF

The process described for the production and recovery of hBDNFmyc was also used to produce and recover recombinant mature full length hBDNF, and yielded protein with similar bioactivity (FIG. 9). The construction of plasmid pRPN149 (FIG. 10), which expresses a LamB1-hBDNF fusion protein, is analogous to the construction of pRPN121. The synthetic LamB1 DNA fragment, described above, was cloned into the SphI and SpeI restriction sites of pRPN09 (Regeneron Pharmaceuticals, Inc.) resulting in plasmid pRPN31. The mature hBDNF DNA sequence was PCR amplified from pCDM8-hBDNF (Regeneron Pharmaceuticals, Inc.) using oligonucleotide primers N1-hBDNF (5'-ACTCTGACCC TGCCCGCCGA GGGGAGCTG-3') (SEQ ID NO: 18) and C1-hBDNF (5'-GCGCGGATCC CTATCTTCCC CTTTTAATGG TCAATGTAC-3') (SEQ ID NO: 19) This DNA fragment was cloned into SmaI and BamHI sites of pRPN31 resulting in plasmid pRPN34. The HindIII-BamHI fragment including the LamB1-hBDNF fusion gene was subsequently cloned into the HindIII-BamHI restriction sites of pRPN52 (described above) resulting in plasmid pRPN66. The NruI-PvuII deletion of pBR322 sequences resulting in higher copy number (described above) was made in pRPN66 resulting in plasmid pRPN149. In this plasmid, expression of LamBi-hBDNF is under control of lacUV5 and the T7 φ1.1 promoter and ribosome binding site. Plasmid pRPN149 has been deposited with the ATCC and has been assigned Accession No: 75027.

We transformed E. coli I$^q$FW3110 with pRPN149. Then we produced and recovered recombinant hBDNF by the procedure described in Example 7.

8. EXAMPLE: PRODUCTION AND RECOVERY OF RECOMBINANT hNT-3

Human NT-3 is produced and recovered by processes similar to those we described for hNGF and hBDNF.

A DNA sequence encoding mature full length hNT-3 is PCR amplified from a cDNA library from human brain cells (Hohn et al., 1991, WO 91/03569, incorporated herein by reference). The oligonucleotide primers EVD-45 (5'-CCTATGCAGA GCATAAGAGT CACCGAGGA-3') ( SEQ ID NO: 20) and EVD-7 (5'-GTAAGGGCGG CCGAAGTTTA ATAAA-TAAAG GTC-3') (SEQ ID NO: 21) are used. These primers are derived from the DNA sequence for rat NT-3 (Maisonpierre et al., Science 247:1446–1451). The sense primer is nearly identical to the human NT-3 sequence. The antisense primer hybridizes approximately one hundred base pairs downstream of the termination codon of the human gene.

This DNA fragment has a C-terminal EagI restriction site suitable for insertion into BalI and EagI sites of pRPN88, where it would replace the hBDNF DNA sequence. The resulting plasmid is used to transform E. coli I<sup>q</sup>FW3110. Then recombinant hNT-3 is produced and recovered as in Example 7. We expect recombinant hNT-3 purified from E-coli to exhibit neurotrophin activity similar to that described by Hohn et al., 1991, (WO 91/03569).

9. EXAMPLE: PRODUCTION AND RECOVERY OF RECOMBINANT hNT-4 FROM E. COLI

9.1. CONSTRUCTION OF pRG173

The DNA sequence encoding the putative mature region of the human NT-4 (hNT-4) gene was amplified by PCR from NT-4 HG7-2 DNA, using the N1-NT4 (5'-CCGGGGTCTCTGAAACTGCACCAGC-GAGTCG-3') [SEQ ID NO: 24] and C1-NT4 (5'-GGTGCAGTTTCAGAGACCC-CCATACGCCGGCTGCGGTTGGC-3 ') [SEQ ID NO: 25] oligonucleotides as primers. The C1-NT4 oligonucleotide generates an EagI restriction site 3' to the NT-4 gene. The PCR generated fragment was digested with EagI and cloned into MscI-EagI digested pRG91. The resulting plasmid, pRG173, consisted of the LamB signal sequence fused to the mature region of hNT-4 (the glycine at amino acid residue 81 in the HG7-2 translated sequence) under the transcriptional control of the lacUV5 and T7 $\phi$1.1 promoters and the translational control of the T7 $\phi$1.1 ribosome binding site. This plasmid also possessed the rop1 deletion which increases plasmid copy number. The construction was confirmed by restriction enzyme analysis of purified plasmid DNA, DNA sequence analysis of the purified plasmid, in vitro synthesis of a protein of the approximate size estimated to be encoded by pRG173, and in vivo synthesis of a protein of the appropriate size estimated to be encoded by pRG173 and possessing neurite outgrowth stimulating activity (see discussion, supra), and having the appropriate N-terminus as determined by amino acid sequencing (GVSETAPAE [SEQ ID NO: 25]).

9.2. PURIFICATION OF HUMAN NT-4 EXPRESSED IN E. COLI RFJ26/pRG173

A 5 ml culture of pRG173 transformed in E. coli strain RFJ26 was grown overnight in LB medium supplemented with 100 mg/L ampicillin at 37° C. with aeration. The overnight culture was diluted into 500 ml LB and grown to OD$_{590}$=5.3 at which time the expression of hNT-4 was induced by the addition of lactose to 1% (w/v) and the culture was grown overnight with aeration. Cells were then collected by centrifugation and frozen at 70° C. The cell pellet (7.2 grams) was thawed and resuspended in 73 ml of 200 mM Tris-HCl, pH 8.0, 50 mM EDTA and lysed by 3 sequential passes through the STANSTED® cell disrupter. The lysate was then centrifuged at 26,000×g for 10 minutes, yielding 83 ml of supernatant containing the soluble fraction. The soluble fraction was dialyzed against 50 mM Tris-HCl, pH 8.5 at 4° C. for 5 hrs then diluted 10-fold with 20 mM MES, pH 6.0 and loaded on a Fast S-Sepharose column equilibrated with 20 mM MES, pH 6.0 and eluted with 1M NaCl in 20 mM MES, pH 6.0. Recombinant human NT-4 protein that stimulated E8 DRG outgrowth was recovered in the 1M NaCl wash.

The insoluble fraction was resuspended and homogenized in 83 ml 8M guanidinium-HCl, 50 mM Tris-HCl, pH 8.5, 10 mM NaCl, 1 mM EDTA. The insoluble fraction was dialyzed against 7M urea, 50 mM Tris-Cl, pH 8.5, and loaded onto a Fast DEAE-Sepharose column equilibrated in 7M urea, 50 mM Tris-Cl, pH 8.5. The breakthrough fractions were collected and dialyzed against 7M urea, 100 mM histidine, pH 5.5, 1 mM EDTA and loaded on a Fast S-Sepharose column equilibrated in 7M urea, 100 mM histidine, pH 5.5, 1 mM EDTA, hNT-4 was eluted with a 0–1M NaCl gradient in the same buffer. Fractions containing hNT-4 were pooled and dialyzed against 100 mM histidine, pH 5.5, 1 mM EDTA. Approximately 95% of the hNT-4 protein fractionated with the insoluble material.

9.3. PREPARATION OF ENRICHED MOTOR NEURON CULTURES

Embryos (E14) from Sprague-Dawley rats (HSD or Zivic-Miller) were used for these experiments. Pregnant rats were sacrificed by carbon dioxide asphyxiation, and embryos were rapidly removed and placed in ice-cold medium for further dissection. Spinal cords were removed aseptically from rat embryos of 14 days gestation. The spinal cord was severed caudal to the bulb (at the level of the first dorsal root ganglion), freed of sensory ganglia and adhering meninges. The cord was then subdivided into ventral and mediodorsal segments for separate cultures. The ventral spinal cord tissues were diced into small pieces and incubated in 0.1% trypsin (GIBCO) and 0.01% deoxyribonuclease type 1 (Sigma) in PBS at 37° C. for 20 minutes. Trypsin solution was then removed, rinsed and replaced with medium consisting of 45% Eagle's minimum essential medium (MEM), 45% Ham's nutrient mixture F12 (F12), 5% heat inactivated fetal.calf serum (GIBCO), 5% heat inactivated horse serum (GIBCO), glutamine (2 mM), penicillin G (0.5 U/ml), and streptomycin (0.5 ug/ml). The tissue was then mechanically dissociated by gentle trituration through a Pasteur pipet, and the supernatants were pooled and filtered through a nylon fiber (Nitex, Tetko; 40 μm). The filtered cell suspension were then subjected to a modification of the fraction procedure described by Schnaar and Schaffner (1981, J. Neurosci. 1:204–217). All steps were carried out at 4° C. Metrizamide was dissolved in F12:MEM (1:1) medium, and a discontinuous gradient was established which consisted of a 18% metrizamide cushion (0.5 ml), 3 ml of 17% metrizamide, 3 ml of 12% metrizamide, and 3 ml of 8% metrizamide was prepared. The filtered ventral spinal cord cell suspension (2.5 ml) obtained as described above was layered over the step gradient, the tube was centrifuged at 2500 g for 15 minutes using a swing-out rotor (Sorvall HB4). Centrifugation resulted in three layers of cells: fraction I (at 0–8% interface), fraction II (at 8–12% interface), and fraction III (at 12–17% interface). The cells from each interface were removed in a small volume (about 1 ml), rinsed twice with serum-free defined medium consisting of 50% F12 and 50% MEM, supplemented with glutamine (2 mM), insulin (5 ug/ml), transferrin (100 ug/ml), progesterone (20 nM), putrescine (100 uM), and sodium selenite (30 nM) (Bottenstein and Sato, 1979, PNAS 76:514–517). Viable cell count was obtained by hemocytometer counting in the presence of trypan blue. Fractionated ventral spinal cord cells (enriched with motorneurons) were then plated at a density of 100,000 cells/$cm^2$ in 6 mm wells precoated with poly-L-ornithine (Sigma: 10 μg/ml) and laminin (GIBCO: 10 μg/ml). Treatment with NT-4 was given on the day of plating. Cultures were maintained in serum-free defined medium at 37° C. in 95% air/5% $CO_2$ atmosphere at nearly 100% relative humidity. On day 2 (48 hours), cells were harvested for measurements of choline acetyltransferase (CAT; Fonnum, 1975, J. Neurochem. 24:407–409.

9.4. RESULTS

The recombinant human NT-4 protein recovered from the 1 m NaCl wash of the soluble fraction was assayed for activity in dissociated motor neuron cultures prepared as described supra at Example Section 9.3, and in other assays. Addition of recombinant human NT-4 at a 1:20 dilution resulted in a 3.6 fold increase in choline acetyltransferase activity in the motor neuron enriched culture 48 hours after treatment. The 3.6 fold increase was measured in relation to untreated (C-NT) and buffer (C-Buffer) controls (FIG. 13).

9.5. DISCUSSION

Subcloning the NT-4 coding region of bacteriophage HG7-2 downstream from the LAC UV5 and T7φ1.1 promoters, the T7φ1.1 ribosome binding site and the LamB signal sequence resulted in plasmid pRG173. Transformation of pRG173 into the E. coli strain RFJ26 and induction of large scale cultures of pRG173/RFJ26 resulted in the expression of a biologically active form of recombinant human NT-4. The ability to express a biologically active form of human NT-4 in an recombinant prokaryotic expression system substantially increases the ease at which the production of human recombinant NT-4, peptides or derivatives thereof may be scaled up for both therapeutic and diagnostic applications.

The present example thus teaches that a DNA sequence encoding a human NT-4 is amenable to transcription and translation in a prokaryotic system such that human NT-4 is expressed and the biologically active form is amenable to purification schemes such that the activity remains subsequent to purification.

10. DEPOSIT OF MICROORGANISMS

The recombinant DNA molecules pRPN133 (hNGF), pRPN121 (hBDNFmyc) and pRPN149 (hBDNF) were deposited on Jun. 7, 1991, pRG173 (NT-4) on Oct. 28, 1991 and the recombinant bacteriophage HG7-2 on Aug. 22, 1991 with the American Type Culture Collection, 12301 Parklawn Drive, Rockville, Md. 20852, under the Budapest Treaty on the International Recognition of the Deposit of Microorganisms for the purposes of Patent Procedure, and assigned the indicated accession number.

| RECOMBINANT DNA MOLECULE | ATCC ACCESSION NO. |
|---|---|
| pRPN133 (hNGF) | 75029 |
| pRPN121 (hBDNFmyc) | 75028 |
| pRPN149 (hBDNF) | 75027 |
| pRG173 (hNT-4) | 75131 |
| HG7-2 (human NT-4 genomic clone) | 75070 |

The present invention is not to be limited in scope by the deposited microorganisms or the specific embodiments described herein. Indeed, various modifications of the invention in addition to those described herein will become apparent to those skilled in the art from the foregoing description and accompanying figures. Such modifications are intended to fall within the scope of the appended claims.

Various publications have been cited herein which are incorporated by reference in their entireties.

While we have hereinbefore described a number of embodiments of this invention, it is apparent that our basic embodiments can be altered to provide other embodiments which utilize the processes and compositions of this invention. Therefore, it will be appreciated that the scope of this invention includes all alternative embodiments and variations which are defined in the foregoing specification and by the claims appended hereto; and the invention is not to be limited by the specific embodiments which have been presented herein by way of example.

---

We claim:

1. A modified LamB signal sequence gene comprising a DNA molecule (SEQ ID NO: 3) encoding a LamB signal sequence which has been altered to encode fourteen hydrophobic amino acids in the hydrophobic core region.

2. The gene of claim 1 wherein the hydrophobic core region of the LamB signal sequence contains fourteen hydrophobic amino acids, comprising a peptide having the sequence LAVL (SEQ ID NO: 6).

3. A fusion gene for expression of a neurotrophin protein comprising a controllable expression control DNA sequence operatively linked to a second DNA sequence encoding, from 5′ to 3′ the signal sequence of claim 2 that is linked in-frame with a third DNA sequence encoding a neurotrophin protein.

4. A modified LamB signal sequence gene comprising a DNA sequence encoding a modified LamB signal sequence having a hydrophobic core region of 11–16 hydrophobic amino acid residues.

5. A process for producing a recombinant neurotrophin comprising the steps of culturing E. coli host cells transformed with a recombinant DNA molecule comprising an expression control sequence operatively linked to a fused gene consisting of, from 5′ to 3′ the LamB signal sequence gene of claim 1 or claim 4 joined in-frame with a neurotrophin encoding sequence, under conditions such that said neurotrophin is expressed by said E. coli host cells; and recovering the expressed neurotrophin.

6. The process of claim 5 wherein the neurotrophin is human neurotrophin-4, wherein said human neurotrophin-4 is encoded by a DNA sequence as contained in E. coli plasmid vector, pRG173, as deposited with the ATCC and assigned accession number 75131.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 75 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:1:

```
ATGATGATTA   CTCTGCGCAA   ACTTCCTCTG   GCGGTTGCCG   TCGCAGCGGG   CGTAATGTCT        60

GCTCAGGCAA   TGGCT                                                                75
```

( 2 ) INFORMATION FOR SEQ ID NO:2:

(i) SEQUENCE CHARACTERISTICS:
  (A) LENGTH: 88 base pairs
  (B) TYPE: nucleic acid
  (C) STRANDEDNESS: double
  (D) TOPOLOGY: unknown (ii) MOLECULE TYPE: DNA (genomic)

(xi) SEQUENCE DESCRIPTION: SEQ ID NO:2:

```
CATGATGATC ACACTGCGTA AGCTTCCGCT AGCTGTAGCA GTAGCAGCAG GTGTAATGTC    60
TGCACAGGCC ATGGCCCGGG ATCCCTAG                                       88
```

(2) INFORMATION FOR SEQ ID NO:3:

(i) SEQUENCE CHARACTERISTICS:
    (A) LENGTH: 96 base pairs
    (B) TYPE: nucleic acid
    (C) STRANDEDNESS: double
    (D) TOPOLOGY: unknown (ii) MOLECULE TYPE: DNA (genomic)

(xi) SEQUENCE DESCRIPTION: SEQ ID NO:3:

```
CATGATGATC ACACTGCGTA AGCTTCCGCT AGCTGTAGCA GTAGCAGCAG GTGTAATGTC    60
TGCACAGGCC ATGGCCAGTC GGCCGAGGAT CCCTAG                              96
```

(2) INFORMATION FOR SEQ ID NO:4:

(i) SEQUENCE CHARACTERISTICS:
    (A) LENGTH: 108 base pairs
    (B) TYPE: nucleic acid
    (C) STRANDEDNESS: double
    (D) TOPOLOGY: unknown (ii) MOLECULE TYPE: DNA (genomic)

(xi) SEQUENCE DESCRIPTION: SEQ ID NO:4:

```
CATGATGATC ACACTGCGTA AGCTTCCGCT AGCAGTACTG CTAGCTGTAG CAGTAGCAGC    60
AGGTGTAATG TCTGCACAGG CCATGGCCAG TCGGCCGAGG ATCCCTAG                108
```

(2) INFORMATION FOR SEQ ID NO:5:

(i) SEQUENCE CHARACTERISTICS:
    (A) LENGTH: 108 base pairs
    (B) TYPE: nucleic acid
    (C) STRANDEDNESS: double
    (D) TOPOLOGY: unknown (ii) MOLECULE TYPE: DNA (genomic)

(xi) SEQUENCE DESCRIPTION: SEQ ID NO:5:

```
CATGATGATC ACACTGCGTA AGCTTCCGCT AGCAGTACTG CTAGCTGTAG CAGTAGCAGC    60
AGGTGTAATG TCTGCACAGG CCATGGCCAG TCGGCCGAGG ATCCCTAG                108
```

(2) INFORMATION FOR SEQ ID NO:6:

(i) SEQUENCE CHARACTERISTICS:
    (A) LENGTH: 4 amino acids
    (B) TYPE: amino acid
    (C) STRANDEDNESS: single
    (D) TOPOLOGY: unknown (ii) MOLECULE TYPE: protein (xi) SEQUENCE DESCRIPTION: SEQ ID NO:6:

```
Leu Ala Val Leu
 1
```

( 2 ) INFORMATION FOR SEQ ID NO:7:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:7:

AAGCGGTCGA CATCTCATCC AATCTTCCAT AGAGGTGAAT TCTCAGTA    48

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:8:

GGCAGGCGGC CGTCATCTCA CAGCCTTCCT GCTG    34

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:9:

CCATTATCGC GACCAGAGGT    20

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:10:

TCTTGCTCGC GAGTTATCAG CTATGCG    27

( 2 ) INFORMATION FOR SEQ ID NO:11:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:11:

ATGATCACAC TGCGTAAGCT TCCGCTAGCT GTAGCAGTAG CAGCAGGTGT AATGTCTGCA    60

CAGGCCATGG CCCGGGATCC    80

( 2 ) INFORMATION FOR SEQ ID NO:12:

( i ) SEQUENCE CHARACTERISTICS:
        ( A ) LENGTH: 88 base pairs
        ( B ) TYPE: nucleic acid ( C ) STRANDEDNESS: single
            ( D ) TOPOLOGY: unknown ( i i ) MOLECULE TYPE: DNA (genomic)

( x i ) SEQUENCE DESCRIPTION: SEQ ID NO:12:

CTAGGGATCC CGGGCCATGG CCTGTGCAGA CATTACACCT GCTGCTACTG CTACAGCTAG    60

CGGAAGCTTA CGCAGTGTGA TCATCATG    88

( 2 ) INFORMATION FOR SEQ ID NO:13:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: unknown ( i i ) MOLECULE TYPE: DNA (genomic)

( x i ) SEQUENCE DESCRIPTION: SEQ ID NO:13:

CATGGCCAGT CGGCCGAG    18

( 2 ) INFORMATION FOR SEQ ID NO:14:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: unknown ( i i ) MOLECULE TYPE: DNA (genomic)

( x i ) SEQUENCE DESCRIPTION: SEQ ID NO:14:

GATCCTCGGC CGACTGGC    18

( 2 ) INFORMATION FOR SEQ ID NO:15:

( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: unknown ( i i ) MOLECULE TYPE: protein ( x i ) SEQUENCE DESCRIPTION: SEQ ID NO:15:

Glu  Gln  Lys  Leu  Ile  Ser  Glu  Glu  Asp  Leu
    1                   5                        10

( 2 ) INFORMATION FOR SEQ ID NO:16:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: unknown ( i i ) MOLECULE TYPE: DNA (genomic)

( x i ) SEQUENCE DESCRIPTION: SEQ ID NO:16:

CCCACTCTGA CCCTGCCCGC CGAGGG    26

( 2 ) INFORMATION FOR SEQ ID NO:17:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: unknown ( i i ) MOLECULE TYPE: DNA (genomic)

( x i ) SEQUENCE DESCRIPTION: SEQ ID NO:17:

GCTATGCGGC CGCTACAGAT CCTCCTC                                          27

( 2 ) INFORMATION FOR SEQ ID NO:18:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: unknown ( i i ) MOLECULE TYPE: DNA (genomic)

( x i ) SEQUENCE DESCRIPTION: SEQ ID NO:18:

ACTCTGACCC TGCCCGCCGA GGGGAGCTG                                        29

( 2 ) INFORMATION FOR SEQ ID NO:19:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: unknown ( i i ) MOLECULE TYPE: DNA (genomic)

( x i ) SEQUENCE DESCRIPTION: SEQ ID NO:19:

GCGCGGATCC CTATCTTCCC CTTTTAATGG TCAATGTAC                             39

( 2 ) INFORMATION FOR SEQ ID NO:20:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: unknown ( i i ) MOLECULE TYPE: DNA (genomic)

( x i ) SEQUENCE DESCRIPTION: SEQ ID NO:20:

CCTATGCAGA GCATAAGAGT CACCGAGGA                                        29

( 2 ) INFORMATION FOR SEQ ID NO:21:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: unknown ( i i ) MOLECULE TYPE: DNA (genomic)

( x i ) SEQUENCE DESCRIPTION: SEQ ID NO:21:

GTAAGGGCGG CCGAAGTTTA ATAATAAAG GTC                                    33

( 2 ) INFORMATION FOR SEQ ID NO:22:

( i ) SEQUENCE CHARACTERISTICS:
  ( A ) LENGTH: 1404 base pairs
  ( B ) TYPE: nucleic acid
  ( C ) STRANDEDNESS: single
  ( D ) TOPOLOGY: unknown ( i i ) MOLECULE TYPE: DNA (genomic)

( i x ) FEATURE:
  ( A ) NAME/KEY: CDS
  ( B ) LOCATION: 460..1104

( x i ) SEQUENCE DESCRIPTION: SEQ ID NO:22:

-continued

```
CTTGTCACCC AGGTGGCAGG GGAGTGGTGC ACTCTCTGCT CACTGCAACC TCGGCCTCCT        60

GGGTTCGAGT GATTCTCCTA CCTCAGCCTA CTGAGTAGCT GGGATTACAG GCGTGCAGCA       120

CTATGCCCGG TTAATTTTGG TATTTTTGGT AGAGATGAGG TTTCACCATG TTGACCAGCT       180

GCTCTGGAAC TCCTGACCTC AAGTCATCCA CCTGCCTCAG CCTCCCAGAG TGCTGGGATT       240

AGAGGTGTGG GGCACAGTGC CTGGCCTGTA GTAGTTGAAT ATTTATTATT AATCTACAAG       300

TTGCGCATTA CGCAAGCCCT AGATATAGGG TCCCCCAAAC TTCTAGAACA AGGGCTTCCC       360

CACAATCCTG GCAGGCAAGC CTCCCCTGGG GTTCCAACT TCTTTCCCCA CTGAAGTTTT        420

TACCCCCTTC TCTAATCCCA GCCTCCCTCT TTCTGTCTC CAG GTG CTC CGA GAG         474
                                              Gln Val Leu Arg Glu
                                                1               5
```

| Codon | Amino acid | Position | | | | | | | | | | Pos |
|---|---|---|---|---|---|---|---|---|---|---|---|---|

```
ATG CTC CCT CTC CCC TCA TGC TCC CTC CCC ATC CTC CTC CTT TTC CTC        522
Met Leu Pro Leu Pro Ser Cys Ser Leu Pro Ile Leu Leu Leu Phe Leu
              10              15                      20

CTC CCC AGT GTG CCA ATT GAG TCC CAA CCC CCA CCC TCA ACA TTG CCC        570
Leu Pro Ser Val Pro Ile Glu Ser Gln Pro Pro Pro Ser Thr Leu Pro
            25              30                  35

CCT TTT CTG GCC CCT GAG TGG GAC CTT CTC TCC CCC CGA GTA GTC CTG        618
Pro Phe Leu Ala Pro Glu Trp Asp Leu Leu Ser Pro Arg Val Val Leu
            40              45                  50

TCT AGG GGT GCC CCT GCT GGG CCC CCT CTG CTC TTC CTG CTG GAG GCT        666
Ser Arg Gly Ala Pro Ala Gly Pro Pro Leu Leu Phe Leu Leu Glu Ala
        55              60              65

GGG GCC TTT CGG GAG TCA GCA GGT GCC CCG GCC AAC CGC AGC CGG CGT        714
Gly Ala Phe Arg Glu Ser Ala Gly Ala Pro Ala Asn Arg Ser Arg Arg
 70          75              80                          85

GGG GTG AGC GAA ACT GCA CCA GCG AGT CGT CGG GGT GAG CTG GCT GTG        762
Gly Val Ser Glu Thr Ala Pro Ala Ser Arg Arg Gly Glu Leu Ala Val
                90              95                  100

TGC GAT GCA GTC AGT GGC TGG GTG ACA GAC CGC CGG ACC GCT GTG GAC        810
Cys Asp Ala Val Ser Gly Trp Val Thr Asp Arg Arg Thr Ala Val Asp
            105             110                 115

TTG CGT GGG CGC GAG GTG GAG GTG TTG GGC GAG GTG CCT GCA GCT GGC        858
Leu Arg Gly Arg Glu Val Glu Val Leu Gly Glu Val Pro Ala Ala Gly
        120             125                 130

GGC AGT CCC CTC CGC CAG TAC TTC TTT GAA ACC CGC TGC AAG GCT GAT        906
Gly Ser Pro Leu Arg Gln Tyr Phe Phe Glu Thr Arg Cys Lys Ala Asp
135             140                 145

AAC GCT GAG GAA GGT GGC CCG GGG GCA GGT GGA GGG GGC TGC CGG GGA        954
Asn Ala Glu Glu Gly Gly Pro Gly Ala Gly Gly Gly Gly Cys Arg Gly
150                 155                 160             165

GTG GAC AGG AGG CAC TGG GTA TCT GAG TGC AAG GCC AAG CAG TCC TAT       1002
Val Asp Arg Arg His Trp Val Ser Glu Cys Lys Ala Lys Gln Ser Tyr
                170             175                 180

GTG CGG GCA TTG ACC GCT GAT GCC CAG GGC CGT GTG GGC TGG CGA TGG       1050
Val Arg Ala Leu Thr Ala Asp Ala Gln Gly Arg Val Gly Trp Arg Trp
            185             190                 195

ATT CGA ATT GAC ACT GCC TGC GTC TGC ACA CTC CTC AGC CGG ACT GGC       1098
Ile Arg Ile Asp Thr Ala Cys Val Cys Thr Leu Leu Ser Arg Thr Gly
        200             205                 210

CGG GCC TGAGACCCAT GCCCAGGAAA ATAACAGAGC TGGATGCTGA GAGACCTCAG        1154
Arg Ala
    215

GGATGGCCCA GCTGATCTAA GGACCCCAGT TTGGGAACTC ATCAAATAAT CACAAAATCA     1214

CAATTCTCTG ATTTTGAGCT CAATCTCTGC AGGATGGGTG AAACCACATG GGTTTTGGA      1274

GGTTGAATAG GAGTTCTCCT GGAGCAACTT GAGGGTAATA ATGATGATGA TATAATAATA     1334

ATAGCCACTA TTTACTGAGT GTTTACTGTT TCTTATCCCT AATACATAAC TCCTCAGATC     1394
```

AACTCTCATG                                                                                              1404

( 2 ) INFORMATION FOR SEQ ID NO:23:

( i ) SEQUENCE CHARACTERISTICS:
        ( A ) LENGTH: 215 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:23:

```
Gln Val Leu Arg Glu Met Leu Pro Leu Pro Ser Cys Ser Leu Pro Ile
 1               5                   10                  15

Leu Leu Leu Phe Leu Leu Pro Ser Val Pro Ile Glu Ser Gln Pro Pro
            20                  25                  30

Pro Ser Thr Leu Pro Pro Phe Leu Ala Pro Glu Trp Asp Leu Leu Ser
            35              40                  45

Pro Arg Val Val Leu Ser Arg Gly Ala Pro Ala Gly Pro Pro Leu Leu
        50              55              60

Phe Leu Leu Glu Ala Gly Ala Phe Arg Glu Ser Ala Gly Ala Pro Ala
65              70                  75                      80

Asn Arg Ser Arg Arg Gly Val Ser Glu Thr Ala Pro Ala Ser Arg Arg
                85                  90                  95

Gly Glu Leu Ala Val Cys Asp Ala Val Ser Gly Trp Val Thr Asp Arg
            100             105                 110

Arg Thr Ala Val Asp Leu Arg Gly Arg Glu Val Glu Val Leu Gly Glu
            115             120                 125

Val Pro Ala Ala Gly Gly Ser Pro Leu Arg Gln Tyr Phe Phe Glu Thr
    130             135                 140

Arg Cys Lys Ala Asp Asn Ala Glu Glu Gly Gly Pro Gly Ala Gly Gly
145                 150                 155                 160

Gly Gly Cys Arg Gly Val Asp Arg Arg His Trp Val Ser Glu Cys Lys
                165                 170                 175

Ala Lys Gln Ser Tyr Val Arg Ala Leu Thr Ala Asp Ala Gln Gly Arg
            180                 185                 190

Val Gly Trp Arg Trp Ile Arg Ile Asp Thr Ala Cys Val Cys Thr Leu
            195                 200                 205

Leu Ser Arg Thr Gly Arg Ala
            210             215
```

( 2 ) INFORMATION FOR SEQ ID NO:24:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:24:

CCGGGGTCTC TGAAACTGCA CCAGCGAGTC G                                                                        31

( 2 ) INFORMATION FOR SEQ ID NO:25:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: unknown ( i i ) MOLECULE TYPE: DNA (genomic)

-continued ( x i ) SEQUENCE DESCRIPTION: SEQ ID NO:25:

GGTGCAGTTT CAGAGACCCC CATACGCCGG CTGCGGTTGG C 41